United States Patent
Giungo et al.

[11] Patent Number: 5,868,728
[45] Date of Patent: *Feb. 9, 1999

[54] MEDICAL LINEAR ACTUATOR FOR SURGICAL DELIVERY, MANIPULATION, AND EXTRACTION

[75] Inventors: John Giungo, Norristown, Pa.; Daniel B. Schein, Los Angeles, Calif.

[73] Assignee: Photogenesis, Inc., Los Angeles, Calif.

[ * ] Notice: The term of this patent shall not extend beyond the expiration date of Pat. No. 5,817,075.

[21] Appl. No.: 395,701

[22] Filed: Feb. 28, 1995

[51] Int. Cl.$^6$ .............................. A61B 17/00; A61F 11/00
[52] U.S. Cl. ................................................................ 606/1
[58] Field of Search ................................ 606/1, 106, 108, 606/127, 128, 198, 205, 214, 167, 171, 174, 185; 604/19, 22, 35, 208; 128/DIG. 1, DIG. 7

[56] References Cited

U.S. PATENT DOCUMENTS

| | | |
|---|---|---|
| 3,934,591 | 1/1976 | Gleason . |
| 4,014,342 | 3/1977 | Staub, et al. . |
| 4,304,866 | 12/1981 | Green et al. . |
| 4,418,691 | 12/1983 | Yannas et al. . |
| 4,428,748 | 1/1984 | Pegman et al. .......................... 606/171 |
| 4,495,288 | 1/1985 | Jarvis, Jr. et al. . |
| 4,499,899 | 2/1985 | Lyons . |
| 4,563,779 | 1/1986 | Kelman . |
| 4,655,774 | 4/1987 | Choyce . |
| 4,662,869 | 5/1987 | Wright . |
| 4,689,399 | 8/1987 | Chu . |
| 4,693,686 | 9/1987 | Sendax . |
| 4,702,697 | 10/1987 | Linkow . |
| 4,727,018 | 2/1988 | Eichner et al. . |
| 4,747,836 | 5/1988 | Luther . |

(List continued on next page.)

FOREIGN PATENT DOCUMENTS

| | | |
|---|---|---|
| 0 340 698 | 11/1989 | European Pat. Off. . |
| 0340698 | 11/1989 | European Pat. Off. . |
| 0428998 | 5/1991 | European Pat. Off. ............... 606/127 |
| 0 535 506 A1 | 4/1993 | European Pat. Off. . |
| 0535506A1 | 4/1993 | European Pat. Off. . |
| 90 912685 | 2/1995 | European Pat. Off. . |
| 90912685 | 2/1995 | European Pat. Off. . |
| 3632786 | 3/1988 | Germany .............................. 606/127 |
| 40 04 921 A1 | 8/1991 | Germany . |
| 4004921A1 | 8/1991 | Germany . |
| WO 91/02499 | 3/1991 | WIPO . |
| WO91/02499 | 3/1991 | WIPO . |
| WO 92/08406 | 11/1991 | WIPO . |
| WO92/08406 | 11/1991 | WIPO . |
| PCT/US96/02267 | 2/1996 | WIPO . |
| PCT/US96/02270 | 2/1996 | WIPO . |

OTHER PUBLICATIONS

LaVail, "Histotypic Organization of the Rat Retina in Vitro", Z. Zellforsch, Springer Verlag, 114:557–579, 1971.

LaVail, "Multiple Growth factors, Cytokines, and Neurotrophins Rescue Photoreceptors from the Damaging Effects of Constant Light", Neurobiology, vol. 89, pp. 11249–11253, Dec. 1992.

LaVail, "RPE Cell Transplantation in RCS Rats: Normal Metabolism in Rescued Photoreceptors", Suppl., Invest. Ophthalmol. Vis. Sci. 33:1127, #4, abs. #2176, Mar. 15, 1992.

Lee, "Transplantation of Cultured Retinal Pigment Epithelium to Rabbit Retina Injured by Sodium Iodate", Suppl., Invest. Ophthalmol. Vis. Sci. 33:1127, #4, abs #2175, Mar. 15, 1992.

(List continued on next page.)

*Primary Examiner*—Glenn K. Dawson
*Attorney, Agent, or Firm*—Daniel B. Schein, Esq.

[57] ABSTRACT

A linear actuator assembly for operating a plurality of surgical tools. The actuator can provide motive power to a plurality of different surgical tools which are attachable to a handpiece associated with the actuator assembly and may be foot pedal operated.

13 Claims, 14 Drawing Sheets

U.S. PATENT DOCUMENTS

| | | |
|---|---|---|
| 4,837,857 | 6/1989 | Scheller et al. . |
| 4,861,339 | 8/1989 | Jonischkeit . |
| 4,868,116 | 9/1989 | Morgan et al. . |
| 4,871,094 | 10/1989 | Gall et al. . |
| 4,900,300 | 2/1990 | Lee . |
| 4,911,161 | 3/1990 | Schechter . |
| 4,927,676 | 5/1990 | Williams . |
| 4,940,468 | 7/1990 | Petillo . |
| 4,963,489 | 10/1990 | Naughton et al. . |
| 4,994,028 | 2/1991 | Leonard et al. . |
| 5,000,963 | 3/1991 | Hefton . |
| 5,019,035 | 5/1991 | Missirilian . |
| 5,184,625 | 2/1993 | Cottone et al. . |
| 5,184,635 | 2/1993 | Cottone et al. ........................ 606/205 |
| 5,220,926 | 6/1993 | Jones . |
| 5,275,607 | 1/1994 | Lo et al. . |
| 5,292,802 | 3/1994 | Rhee et al. . |
| 5,295,967 | 3/1994 | Rondelet et al. . |
| 5,306,260 | 4/1994 | Kanner . |
| 5,308,343 | 5/1994 | Gafner . |
| 5,308,889 | 5/1994 | Rhee et al. . |
| 5,322,504 | 6/1994 | Doherty et al. . |
| 5,322,691 | 6/1994 | Darougar et al. . |
| 5,323,788 | 6/1994 | Silvestrini et al. . |
| 5,324,260 | 6/1994 | O'Neil et al. . |
| 5,326,346 | 7/1994 | Cortes . |
| 5,326,584 | 7/1994 | Kamel . |
| 5,328,481 | 7/1994 | Wang . |
| 5,342,370 | 8/1994 | Simon et al. . |
| 5,346,464 | 9/1994 | Camras . |
| 5,370,658 | 12/1994 | Scheller et al. . |
| 5,374,515 | 12/1994 | Parenteau et al. . |
| 5,409,478 | 4/1995 | Gerry et al. ............................ 606/108 |
| 5,507,807 | 4/1996 | Shippert . |
| 5,533,981 | 7/1996 | Mandro et al. ......................... 604/208 |

OTHER PUBLICATIONS

Li, "Transplantation of Retinal Pigment Epithelial Cells to Immature and Adult Rat Hosts: Short–and Long–term Survival Characteristics", Exp. Eye Res. 47:771–785 (1988).

Li, "Inherited Retinal dystrophy in the RCS Rat: Prevention of Photoreceptor Degeneration by Pigment Epithelial Cell Transplantation", Exp. Eye Res. 47:911–917, (1988).

Li, "Optimal Coditions for Long–term Photoreceptor Cell Rescue in RCS Rats: The Necessity for Healthy RPE Transplants", Exp. Eye Res. 52:669–679, (191).

Liu, "Photoreceptor inner and outer segments in transplanted retina", Soc. Neurosci., 16:405, abs. #171.1, 1990.

Liu, "Transplantation of confluent sheets of adult human RPE", Invest. Ophthalmol. Vis. Sci. 33:1128, #4, abs. #2180, Mar. 15, 1992.

Liu, "Transplantation of confluent sheets of adult human and rat RPE on a thin substrate", Suppl., Invest. Ophthalmol. Vis. 34:1112, abs. #2018–50, 1993.

Lopez, "Transplanted retinal Pigment Epithelium Modifies the Retinal Degeneration in the RCS Rat", Invest. Ophthalmol. & Vis. Sci., 30:586–589, #3, Mar. 1989.

Lopez, "Transplantation of Human RPE Cells into the Monkey", Suppl. Invest. Ophthalmol. Vis. Sci., 31:594, abs #2910–8, 1990.

Lund, "Axonal Outgrowth from Transplanted Retinae is stimulated by Appropriated Target Regions", Suppl., Invest. Opthalmol. Visc., 28:288, abs. #12(1987).

MacLeish, "Growth and Synapse Formation Among Major Classes of Adult Salamander Retinal Neurons in Vitro", Neuron, Vo. 1, pp. 751–760, Oct. 1988.

Mayerson, "An Improved Method for Isolation and Culture of Rat Retinal Pigment Epithelial Cells", Invest. Ophthalmol. & Vis. Sci., 26:1599–1609, Nov. 1985.

McConnell, "Regeneration of ganglion cell axons in the adult mouse retina", Brain Research, 241:362–365 (1982).

Maurice, "Keratoplasty with Cultured Endothelium on Thin Membranes", Arvo Abstracts, Supp. Inv. Ophthalmol. and Vis. Sci., pp. 10, abs #9, Apr. 1979.

McCulley, "Corneal Endothelial Transplantation", Ophthalmol., vol. 87, #3, pp. 194–201, Mar. 1980.

McCulley, "A Gelatin Membrane Substrate for the Transplantation of Tissue Cultured Cells, Transplantation", vol. 29, No. 6, pp. 498–499, Jun. 1980.

Mollenhauer, "Plastic Embedding Mixtures for use in Electron Microscopy", Stain Tech., 39:111–114.

Moritera, Transplants of monolayer retinal pigment epithelium grown on biodegradable membrane in rabbits. Invest. Ophthalmol. Vis. 34: #4, abs. 1919–75, Mar. 15, 1993.

Muller, "Morphology and synaptic inputs to lucifer yellow injected bipolar cells in rat retinal slices", Soc. Neurosci., 17:1013, abs. #403.4, Nov. 10–15, 1991.

Muller, "Rod and cone inputs to bipolar cells in the rat retina", Inves. Ophthalmol. Vis. Sci. 34:984, #4, abs. #1387, Mar. 15, 1993.

Mueller, "Autotransplantation of Retinal Pigment Epithelium in Intravitreal Diffusion Chamber", vol. 80, No. 3, part II Retinal Pigment Epithelium, pp. 530–537, 1993.

Nasir, "Choriocapillaris Atrophy as a Complication of Surgical Excision of Choroidal Neovascular Membranes", Invest. Ophthalmol. Vis. Sci. 34:834, #4, abs. #653, Mar. 15, 1993.

Newsome, "Transplantation of Human Retinal Pigment Epithelium Into Primate Model of Macular Degeneration", Retina Society Meeting, Toronto, Canada, Sep. 1991.

O'Steen, Retinal and Optic Nerve Serotonin and Retinal Degeneration as Influenced by Photoperiod, Exp. Neurology, 27:194–205, 1970.

Petry, "Immunocytochemical Identification of Photoreceptor Populations in the Retinas of Normal and Red–Light–Reared Tree Shrews", Soc. Neuroscience, 18:838, abs #352.9, Oct. 25–30, 1992.

Pfeffer, Improved Methodology for Cell Culture of Human and Monkey Retinal Pigment Epithelium, Chapter 10, Progress in retinal research, vol. 10, pp. 251–291, 1991.

Politi, Generation of Enriched Populations of Cultured Photoreceptor Cells, Invest. Ophthalmol. Vis. Sci., vol. 27, No. 5, pp. 656–665, May, 1986.

Powell, "Controlled release of nerve growth factor from a polymeric implant", Brain Res., 515:309–311, 1990.

Pu, "Biochemical Interruption of Membrane Phospholipid Renewal in retinal Photoreceptor Cells", Jour. of Neurosci., vol. 4, No. 6, pp. 1559–1576, Jun. 1984.

Radel, "Quantification of Light–Activated Pupilloconstriction in Rats Mediated by Intracranially Transplanted Retinae", Suppl. Invest. Ophthalmol. Vis. Sci. 32:983, abs #1550, 1991.

Radtke, "Pharmacological Therapy for Proliferative Vitreoretinopathy", vol. 224 Graefe's Archive Ophthalmol. pp. 230–233, 1986.

Raymond, "Progenitor Cells in Outer Nuclear Layer of Goldfish Retina That Normally Produce Only Rods Produce other Neurons during Retinal Degeneration", Suppl., Invest. Ophthalmol. Vis. Sci. 28:288, abs #13, 1987.

Royo, "Retinal Transplantation from Fetal to Maternal Mammalian Eye", Growth, 23:313–336, 1959.

Adolph; "Function and Structure in Isolated Subretinal Transplants", Invest. Ophthalmol. Vis. Sci. 34:1096, #4, abs. #1933–89, Mar. 15, 1993.

Anderson; "Retinal Detachment in the Cat; The Pigment Epithelial–Photoreceptor Interface", Invest. Ophthalmol. Vis. Schi., vol. 24, pp. 906–926, Jul. 1983.

Aramant; "Xenografting Human Fetal Retina to Adult Rat Retina", Suppl. Invest. Ophthalmol. Vis. Sci., 31:594, abs. #2907–5, 1990.

Aramant; "The Fate of Retinal Ganglion Cells, Retrogradely Labeled with Fluorogold and Transplanted to Rate Retina", Suppl. Invest. Ophthalmol. Vis. Sci., 32:983, abs. #1545, 1991.

Aramant; "Tracing of connections Between Retinal Transplants and Hosts Retina with . . . ", Invest. Ophthalmol. Vis. Sci., 34:1096, #4, abs. #1935–91, Mar. 15, 1993.

Arvo; "Arvo Abstract Packet for Annual Meeting", Sarasota, Florida (May 2–May 7, 1993) Deadline for Abstract Receipt, Dec. 4, 1992.

Arvo; "Arvo Conference Brochure for Annual Meeting", Sarasota, Florida (May 2–May 7, 1993).

Axen; "Chemical Coupling of Peptides and Proteins to Polysaccharides by Means of Cyanogen Halides", nature, 214:1302–1304, Jun. 24, 1967.

"Biodegradable Polymers", Polysciences, Inc., Data Sheet #365, Jan. 1990.

Bhatt; "Transplantation of Human Retinal Pigment Epithelial Cells Into Rabbits", Invest. Ophthalmol. Vis., vol. 4, #4, abs. #1920–76, Mar. 15, 1993.

Bignami; "The Radial Glial of Muller in the Rat Retina and Their Response to Injury. An Immunofluorescence Study with Antibodies to the Glial Fibrillary Acidic (GFA) Protein", Exp. Eye Res., 28:63–69, (1979).

Bjorklund; "Neural Grafting in the Mammalian CNS", Elsevier Science Publishing B.V., Netherlands, Ch. 38, pp. 431–436, 1985.

Bonds; "Visually evoked potentials and deoxyglucose studies of monocularly deprived cats", Suppl., Invest. Ophthalmol. Visual Sci. 18:225, abs. #11, Apr. 1980.

Cameron; "The Cone Photoreceptor Mosaic of the Green Sunfish", Soc. Neuroscience, 18:838, abs. #352.6, Oct. 25–30, 1992.

Cuatrecasas; "Selective Enzyme Purification by Affinity Chromatography", Biochemistry Cuatrecasas et al., 61:636–643, Aug. 9, 1968.

Custits; "Clinical Angiographic and Histopathologic Correlations in Surgically removed Subfoveal Choroidal Neovascularization", Invest. Ophthalmol. Vis. Sci., 34:834, #4, abs #651, Mar. 15, 1993.

del Cerro; "Intraocular Retinal Transplants", Invest. Ophthalmol, Vis. Sci., vol. 26, pp. 1182–1185, Aug. 1985.

del Cerro; "Intraretinal transplantation of fluorescently labeled retinal cell suspensions", Neurosci. Lt., 92 pp. 21–26, (1988).

del Cerro, "Retinal Transplants", Progress in Retinal Research vol. 9, chapter 6, pp. 229–269, 1990.

del Cerro, "Selective Transplantation of Enriched Cell Populations Derived from Immature Rat Retina", Supp. Invest. Ophthalmol. Visual Sci., 30:208, abs. #6, 1989.

Del Priore, "Transplantation of Retinal Pigment Epithelium (RPE) Onto Bruch's Memebrane in Organ Culture", Suppl., Invest. Ophthalmol. Vis. Sci. 33:1127, #4, abs. #2174, Mar. 15, 1992.

Del Priore, "Experimental and surgical aspects of retinal pigment epithelial cell transplantation", Eur. J. Implant Ref. Surg. 5:128–131, Jun. 1993.

Del Priore, "Differential ability of aged versus young human Bruch's Membrane to support repopulation by health RPE", Invest. Ophthalmol. Vis. Sci. 34:834, #4, abs #652, Mar. 15, 1993.

Du, "Long Term Survival of Infant Versus Adult Photoreceptor Transplants Labeled by Tritiated Thymidine", Suppl. Invest. Ophthalmol. Vis. Sci. 32:983, abs #1546, 1991.

Du, "Neonatal Mouse Photoreceptor Transplants Replace the Photoreceptor Layer of the Host", Invest Ophthalmol.Vis. Sci. 34:1096, #4, abs. #1934–90, Mar. 15, 1992.

Edwards, "Light–Regulated Protein Phosphatase Activity in Limulus Ventral Photoreceptors", Soc. Neurosci. 16:405, abs. #171.6, 1990.

Faktorovich, "Photoreceptor Degeneration in Inherited Retinal Dystrophy Delayed by Basic Fibrolast Growth Factor", Nature, 347:83–86, Sep. 6, 1990.

Faktorovich, "Basic Fibroblast Growth Factor and Local Injury Protect Photoreceptors from Light Damage in the Rat", vol. 12(9) Journal of Neuroscience pp. 3554–3567, Sep. 1992.

Fang, "Development of a surgical procedure and instrument for transplantation of extended gelatin sheets to the subretinal space", Invest. Ophthalmol. Vis. Sci. 34:1096, #4, abs. #1918–1974, Mar. 15, 1993.

Ferguson, "Effect of genetic disparity on photoreceptor transplant survival", Invest. Ophthalmol. Vis. Sci. 32:983, #4, abs #1549, Mar. 15, 1991.

Fischer, "Photoreceptor Topography in the Retinae of Anubis Baboons", Soc. Neuroscience 18:838, abs. #352.7, Oct. 25–30, 1992.

Garcia, "Comparison of Allogeneic and Syngeneic RPE Transplants in Renal Subcapsular Space", Invest Ophthalmol. Vis. 34:1112, abs. #2017–2049, 1993.

Gao, "Low immunogenicity of neonatal murine photoreceptor cells for cytotoxic lymphocytes in mice", Invest. Ophthalmol. Vis. Sci. 33:1285, #4, abs #2963, Mar. 15, 1992.

Gelanze, "Survival of Photoreceptors Transplanted to the Subretinal Space of Adult RCS Rats", Suppl. Invest. Ophthalmol. Visual Sci., 30:208, abs. #8, (1989).

Gouras, "Reconstruction of Degenerate rd Mouse Retina by Transplantation of Transgenic Photoreceptors", Invest. Ophthal. & Vis. Sci., vol. 33/9, pp. 2579–2586, Aug. 1992.

Gouras, "Transplanted Photoreceptors From Mature Outer Segments in Degenerate rd Mouse Retina", Invest. Ophthalmol. Vis. Sci. 33:1128, #4, abs #2180, Mar. 15, 1992.

Gouras, "Anatomy and Physiology of Photoreceptor Transplants in Degenerate C3H Mouse Retina", Invest. Ophthalmol. Vis. Sci. 34:1096, #4, abs. #1938–94, Mar. 15, 1993.

Hicks, "Different Rhodopsin Monoclonal Antibodies Reveal Different Binding patterns on Developing and Adult Rat Retina", Jour. of Histochemistry & Cytochemistry, vol. 35, No. 11, pp. 1317–1328, (1987).

Honig, "Fluorescent Carbocyanine Dyes Allow Living Neurons of Identified Origin to be Studied in Long–term Cultures", Jour. of Cell Biology, 103:171–187, Jul. 1986.

Hughes, "Whole Cell Recordings of Isolated Retinal Pigment Epithelial Cells of the Frog", Soc. Neurosci. Abstr. 17:1301, abs. #360.18, 1987.

Hughes, "Transplantation of Retinal Photoreceptors to Dystrophic Retina", Society Sci. Abstr. 1277, abs. #511–16, Nov. 1988.

Hughes, "Transplanted Photoreceptors Form Synapses in Light–Damaged Retina", Suppl. Invest. Ophthalmol. Vis. Sci., 31:594, abs. #2908–6, 1990.

Hughes, "Differential survival of sensory elements in intracranial otic transplants", Soc. Neurosci., 17:1138, abs. #452.12, Nov. 10–15, 1991.

Hughes, "Quantification of synapses in light–damaged retina reconstructed by transplantation of photoreceptors", Invest. Ophthalmol. Vis. Sci., #4, 33:1058, abs. 1832–3, Mar. 15, 1992.

Hughes, "Explorations of optic transplantation", Experimental Neurology, 115:37–43, 1992.

Jacobs, "An Ultraviolet–Sensitive Cone in the Gerbil Retina", Soc. Neuroscience, 18:838, abs #352.10, Oct. 25–30, 1992.

Jiang, "Intraocular Retinal Transplantation in Retinal Degeneration (rd/rd) Murine Strains", Suppl., Invest. Ophthalmol. Visual Sci., 30:208, abs. #5, (1989).

Kaplan, "Retinal pigment epithelium regeneration in the non–human primate", Suppl., Invest. Ophthalmol. Vis. Sci. #4, abs. #2173, Mar. 15, 1992.

Kitchell, "Poly(lactic/glycolic acid) biodegradable Drug–Polymer Matrix Systems", Methods in Enzymology, 112:436–448, Chapter 32, (1985).

Klassen, "Retinal transplants can drive a pupillary reflex in host rat brains", Proc. Natl. Acad. Sci. U.S.A., vol. 84, pp. 6958–6960, Oct. 1987.

Klassen, "Anatomical and Behavioral Correlates of a Xenograft–Mediated Pupillary Reflex", Experimental Neurology 102, 102–108, (1988).

Kordower, "Fetal Monkey Retina Transplanted into Adult Rat Eyes", Supp. Invest. Ophthalmol. Visual Sci., 30:208, abs. #7, (1989).

Kruszewska, "Ultrastructure and Transduction in the Caudal Photoreceptor of Crayfish", Soc. Neurosci. 16:405, abs. #171.5, 1990.

Lane, Transplantation of Retinal Pigment Epithelium Using a Pars Plana Approach, Eye, 3:27–32, 1989.

Sarthy, Isolated Cells from a Mammalian Retina, Brain Research, 176:208–212, 1979.

Schuschereba, "Retinal cell and photoreceptor transplantation between adult New Zealand Red Rabbit Retinas", Experimental Neurology, 115:95–99, 1992.

Seaton, "Inhibition of Neovascularization by the Transplantation of Healthy Retinal Pigment Epithelial Cells into the RCS Rat", Suppl., Invest. Ophthalmol. Vis. Sci. 32:983, abs #1547, 1991.

Sheedlo, "Photoreceptor Cell Rescue by RPE–Cell Grafts in RCS Rats at Early and Late Stages of Retinal Dystrophy", Suppl., Invest. Ophthalmol. Visual Sci., 30:208, abs #10, 1989.

Sheedlo, Functional and Structural Characteristics of Photoreceptor Cells Rescued in RPE–cell Grafted Retinas of RCS Dystrophic Rats, 48:841–854, 1989.

Shiosaka, "A simple method for the separation of retinal sublayers from the entire retina with special reference to application for cell culture", Jour. Neurosci. Methods, 10:229–235, 1984.

Silverman, "Deoxyglucose mapping of Orientation and spatial frequency in cat visual cortex", Suppl., Invest. Ophthalmol. Visual Sci. 18:225, abs #10, 1980.

Silverman, "Deoxyglucose mapping of orientation in cat visual cortex", Recent Advances in Vision. Optical Society of America Technical Digest, SA13, 1980.

Silverman, "The retinotopic organization of cat striate cortex", Suppl. Invest Ophthalmol. Visual Sci. 22:105, abs. #1, 1982.

Silverman, "Department of Health and Human Services Grant Application, Transplantation of Mammalian Photoreceptors", Martin S. Sivlerman, pp. 1–13, submitted May, 1986, funded by NEI Sep. 11, 1986, Grant No. 1RO3 EY 06943–01.

Silverman, "Department of Health and Human Services Grant Application, Transplantation of Mammalian Photoreceptors", Martin S. Silverman, pp. 1–61, submitted May, 1987, funded by NEI Feb. 16, 1988, Grant No. 1RO1 EY07547–01.

Silverman, Transplantation of retinal photoreceptors to light damaged retina, Suppl., Invest. Ophthalmol. Vis. Sci. 28:288, abs #11, 1987.

Silverman, Transplantation of retinal photoreceptors to light damaged retina: Survival and integration of receptors from a range of postnatal ages, Soc. Neurosci. Abstr. 17:1301, abs. #360.17, 1987.

Silverman, Transplantation of Human Photoreceptors to Light Damaged Retina, Soc. Neurosci. Abstr. 18:1278, abs. #511.17, 1988.

Silverman, "Photoreceptor transplantation in inherited and environmentally induced retinal degeneration: Anatomay, Immunohistochemistry and Function. Inherited and Enviromentally Induced Retinal Degenration", (ed., MM LaVail, RE Anderson, and JG Hollyfield) Alan r. Liss publisher, pp. 687–704, 1989.

Silverman, "Photoreceptor rescue in the RCS rat without pigment epithelium transplantation", Soc. Neurosci., 15:115, abs #51.1, Oct. 29–Nov. 3, 1989.

Silverman, "Transplantation of Photoreceptors to Light Damaged Retina", Invest. Ophthalmol. Vis. Sci., vol. 30, No. 8, 1684–1690, Aug. 1989.

Silverman, Light Dependent Activation of Light Damaged Retina by Transplanted Photoreceptors, Suppl., Invest. Ophthalmol. Visual Sci., 30:208, abs. #9, 1989.

Silverman, "Transplantation of Human and Non–Human Primate Photoreceptors to Damaged Primate Retina", Invest. Ophthalmol. Visual Sci., 31:594, abs #2909–7, 1990.

Silverman, "Photoreceptor rescue in the RCS rat without pigment epithelium transplantation", Curr. Eye Res. 9:183–192, #2, 1990.

Silverman, "Photoreceptor transplantation to dystrophic retina. Retinal Degeneration", (ed. Anderson R.E., La Vail, MM, and Hollyfield J.G.). CRC Press, Inc., Boca Raton, Florida, pp. 321–335, Chapter 29, 1991.

Silverman, Silverman Confidential letter from Central Institute for the Death at Washington University Medical Center, dated Oct. 7, 1991 to Gholam A. Peyman, M.D. and attachments.

Silverman, "Restoration of the pupillary reflex by photoreceptor transplantation", Suppl., Invest. Ophthalmol. Vis. Sci. 32:983, Abs #1548, 1991.

Silverman, Effect of Genetic Disparity on Photoreceptor Transplant Survival, Suppl., Invest. Ophthalmol. Vis. Sci. 32:983, abs #1549.

Silverman, "Photoreceptor transplantation: Anatomic, electrophysiologic and behavioral evidence for the functional reconstruction of retinas lacking photoreceptors". Soc. Neurosci. 17:12, abs. #9.4, Nov. 10–15, 1991.

Silverman, "Photoreceptor transplantation: Anatomic, electrophysiologic and behavioral evidence for the functional reconstruction of retinas lacking photorecptors", Experimental Neurology 115:87–94, 1992.

Silverman, "Rescue of host cones by transplanted donor photoreceptors in the rd mouse", Invest. Ophthalmol. Vis. Sci. 34:1096, #4, abs. #1937–93, Mar. 15, 1993.

Silverman, Transplantation of Retinal Photoreceptors to Light–Damaged Retina, 288 Arvo Abstracts, abs. #11.

Silverman, "A comparison of Ocular Dominance Patterns in Cat and Monkey", Suppl. Invest. Ophthalmol. Visual Sci. 22:12, #3, abs. #13, Mar. 1982.

Simmons, "Physiological Responses in Retinal Transplants and Host Tecta Evoked by Electrical or Photic Stimulation of Transplanted Embryonic Retinae", Soc. Neurosci. Abstr. 10:668, abs #196.5.

Sokoloff, "the [C] Deoxyglucosel Method for the Measurement of Local Cerebral Glucose Utilization: Theory, Prodedure, and Normal Values in the Conscious and Anestherized Albino Rat", Jour. of Neurochem., 28:897–916, 1977.

Solomons, Special Topic M Photochemistry of Vision Organic Chemistry. 5th Ed., Univ. of Fl, Pub. Wiley & Sons, pp. 1168–1171, 1991.

Tien, In Search of A Receptor for Outer Segments in Rat Retinal Pigmented Epithelium, Soc. Neurosci. 16:405, abs #171.3, 1990.

Tootell, "Deoxyglucose mapping of color and spatial frequency organization in monkey and Cat Cortex", Recent Advances in Vision. Optical Society of America Techn. Digest. SA14, 1980.

Tootell, "Color–Dependent Deoxyglucose Patterns Within Macaque Cortex". Arvo Abstracts 226, Suppl., Invest. Ophthalmol. Vis. Sci. pp. 226, abs. #12, Apr. 1980.

Tootell, "2DG study of retinotopic organization in macaque striate cortex", Suppl., Invest. Ophthalmol. Visual Sci. 22:12, #3, abs. #14, Mar. 1982.

Tootell, "Deoxyglucose analysis of retinotopic organization in primate striate cortex", Sci. 218:902–904, Nov. 26, 1982.

Tootell, "Two methods for flat–mounting cortical tissue", Journal Neurosci. Methods, 15:177–190, 1985.

Townes, "Rod Photoreceptors Dissociated from the Adult Rabbit Retina", Jour. of Neuroscience, vol. 8, No. 1, pp. 320–331, Jan. 1988.

Tuliusson, Reversed Ratio of Color Specific Cones in Rabbit Retinal Transplants, Invest. Ophthalmol. Vis. Sci. 34:1096, abs #1936–92, Mar. 1993.

Turner, "Newborn Rat Retinal Cells Transplanted Into a Retinal Lesion Site In Adult Host Eyes", Develop. Brain Research, 26:91–104, (1986).

Valentino, Transplanted photoreceptors form synapses in reconstructed RCS rat retina. Soc. Neurosci., 16:405, abs #171.2, Oct. 28–Nov. 2, 1990.

Valentino, "Photoreceptor rescue in RCS rat and rd mouse by heat shock", Suppl., Invest. Ophthalmol. Vis. Sci., 31:594, abs. #2911–9, 1990.

Valentino, "Photoreceptor sheets isolated form the neonatal rat retina lack synapses and other retinal cells", Soc. Neuroscience. 18:838, abs. #352–8, Oct. 25–30, 1992.

Vinores, "Ultrastructural Localization of RPE Epitopes in In Situ and Clutrued RPE Cells and their Expression in Fibroblasts in Vitreous Culture", Soc. Neurosci. 16:405, abs. #171.4, 1990.

Weiss, Transplanting the Light Fantastic Cells from eye donors may someday restore vision in some blind individuals, Science News, vol. 136, No. 19, pp. 297–300, Nov. 4, 1989.

Wilcheck, "Immobilization of Enzymes and Affinity Ligands onto Agarose Via Stable and Uncharged Carbamate Linkages", Biochem. Int'l. vol. 4, No. 6, pp. 629–635, Jun. 1982.

Wise, Lactic/Glycolic Acid Polymer, Drug Carriers in Biology and Medicine (ed. Gregoriaris) 1979 Chapter 12, pp. 237–270.

Zucker, "Synaptic Microcircuitry of Rat Retinal Transplants Ultrastructural Observations", Suppl., Invest. Ophthalmol. Vis. Sci., 31:594, abs. #2906–4, 1990.

MEDICAL LINEAR ACTUATOR FOR SURGICAL DELIVERY, MANIPULATION, AND EXTRACTION

BACKGROUND OF THE INVENTION

The present invention relates in general to surgical instruments and surgical techniques. More particularly, the present invention is directed to a linear actuator for a multifunctional surgical tool for delivery of grafts, drugs, devices, and for irrigation/aspiration of various parts of the body; as well as surgical manipulation and extraction.

There is a need for a device to deliver, extract, and implant medical devices, drugs, tissue, etc. to various parts of the body. Such a device must be capable of delivering an implant in a target site in the body in a controlled, calibrated fashion where necessary. There is a need for implantation of neural and other living tissue, an increasing number of surgical devices, and drugs. In addition, existing implants frequently require treatment involving manipulation and extraction procedures. By way of non-limiting example, a significant number of patients receive vascular prosthetics, e.g. stents, which are provided by way of a catheter. It is desirable that vascular prosthetics and grafts be expressed from the catheter in a controlled and calibrated fashion. Further, there is a need to alter the position of such prosthetic devices in the body or to extract these devices. Likewise, there is a need to deliver, manipulate, and extract other medical and therapeutic devices.

Many self powered surgical tools have been developed which are capable of performing the previously mentioned tasks. Most of these tools have pneumatic drive means. U.S. Pat. No. 5,019,035 issued to Missirlian et al. discloses one such device. Missirlian describes a pneumatically operated microsurgical cutting instrument. A spring biased inner cutting member moves in a first direction relative to a stationary cutting member in response to the applied air pressure. A spring returns the inner cutting member to its original position. This system, like all pneumatic systems suffers from an inherent hysteresis in the system. This hysteresis limits the control that the operator has over the implement thereby complicating delicate procedures. Also, pneumatic systems tend to impart a "jerky" movement to the implement further affecting the precision and accuracy with which the tool can be effectively used. Finally, the pneumatic systems can be subject to leaky and clogged supply/vacuum lines which can affect performance.

U.S. Pat. No. 4,837,857 issued to Scheller et al. discloses a foot pedal assembly which can be used for remotely controlling a variety of microsurgical instruments. The system employs pneumatic drive means and is thereby subject to the aforementioned drawbacks.

SUMMARY OF THE INVENTION

Among the several objects and features of the present invention may be noted the provision of a microprocessor controlled drive means adaptable for use with a plurality of functional attachments including, but not limited to, cutting tools, grasping tools, and tools useful for implantation of various devices, tissues, grafts, and drugs into the body.

Generally, the microprocessor controlled drive means comprises a source of motive power, a linear actuator, and a microprocessor to selectively apply power to the linear actuator. The microprocessor can control the direction, speed, length of travel, and duration that power is applied to the linear actuator.

The linear actuator of the present invention provides previously unobtainable levels of accuracy and precision in the controlled surgical delivery and manipulation of materials and devices, particularly in surgery beneath and around the retina, other parts of the eye, and in remote portions of blood vessels from the surgical delivery incision.

The linear actuator may be a cable or thin tubular plunger disposed within a second tubular body and capable of relative axial movement therein. In alternative embodiments, the plunger may be actuated manually, by a spring loaded foot pedal assembly, or by a foot pedal operated ratchet wheel assembly.

Other objects and features of the invention will be in part apparent and in part pointed out hereinafter with reference to the following description of non-limiting embodiments.

DETAILED DESCRIPTION

Figure 1:
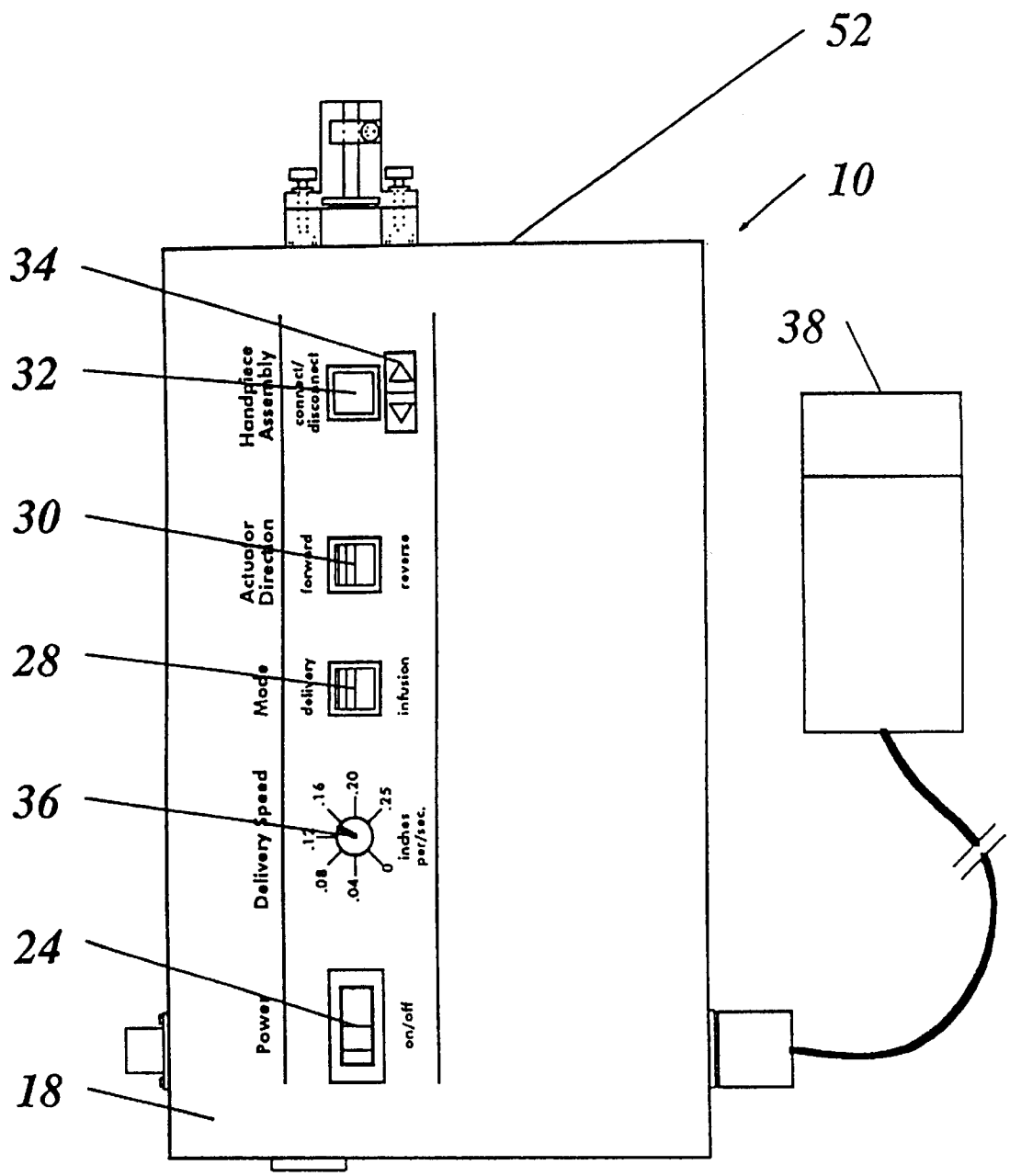
FIG. 1 is a top elevation view of a housing for a source of motive power for the surgical instrument.
Figure 2:
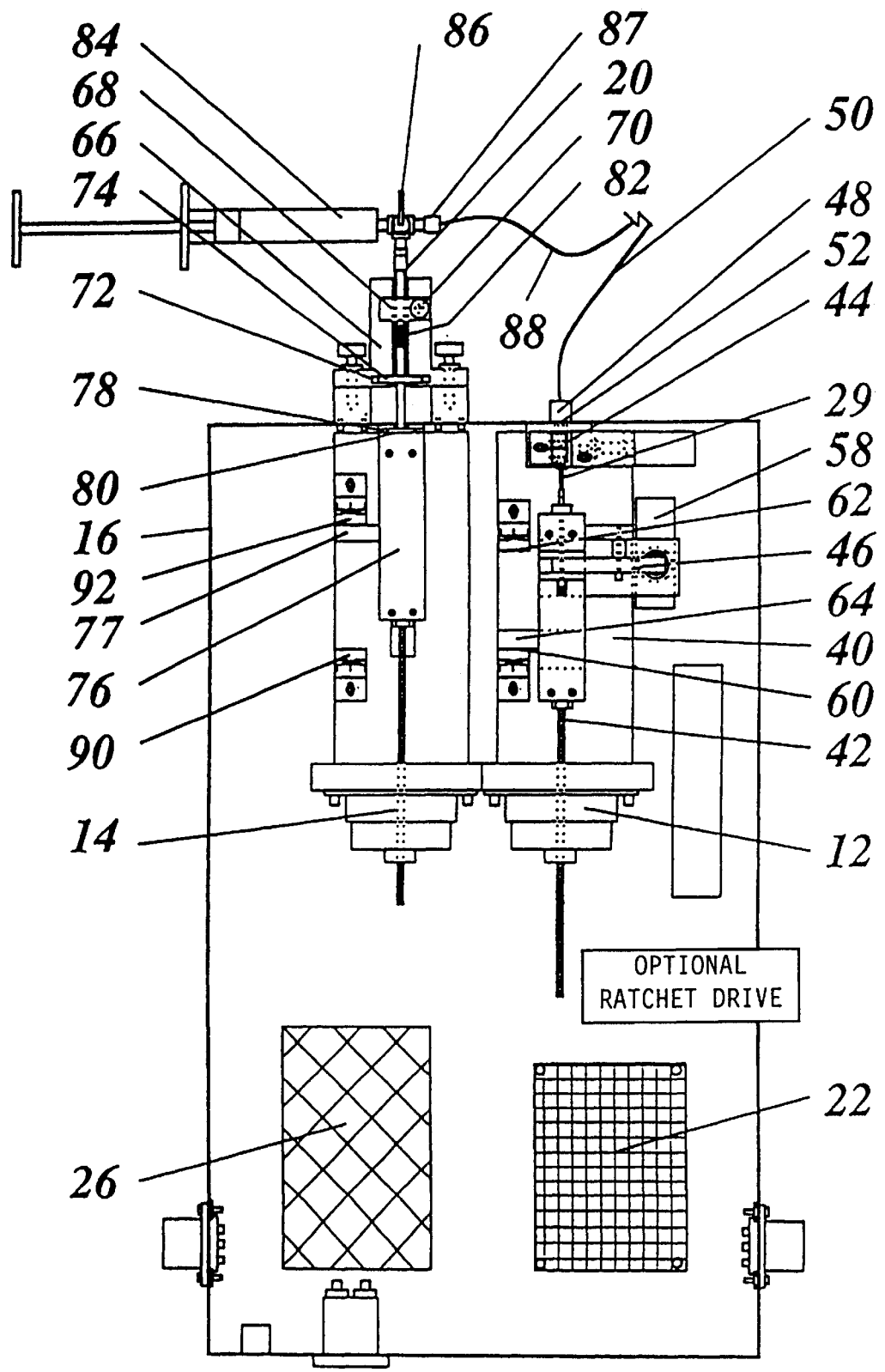
FIG. 2 is a top plan view of the interior components of FIG. 1.
Figure 3A:
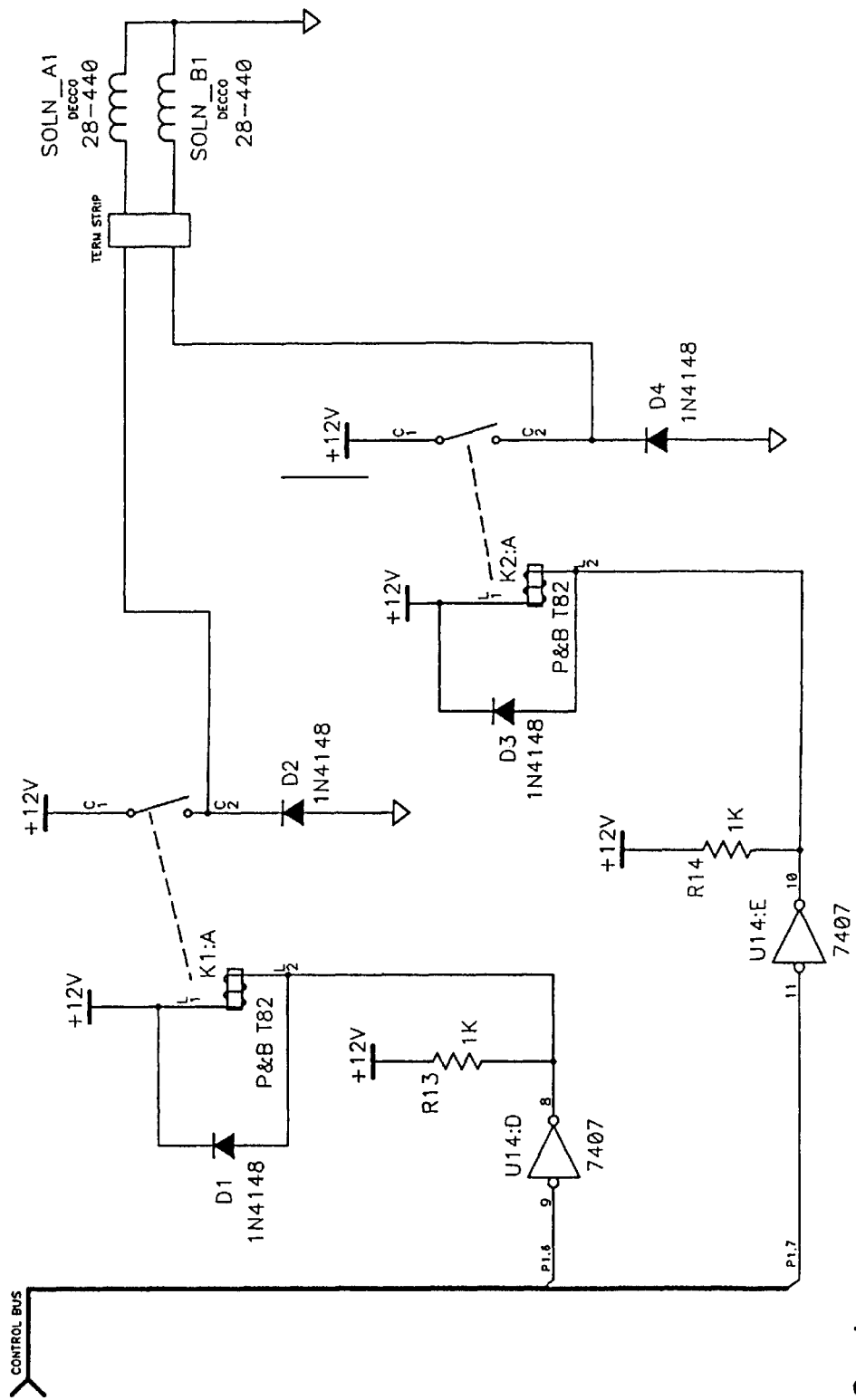
FIG. 3 is a schematic of the control circuitry used to selectively supply power to the surgical instrument.
Figure 3B:
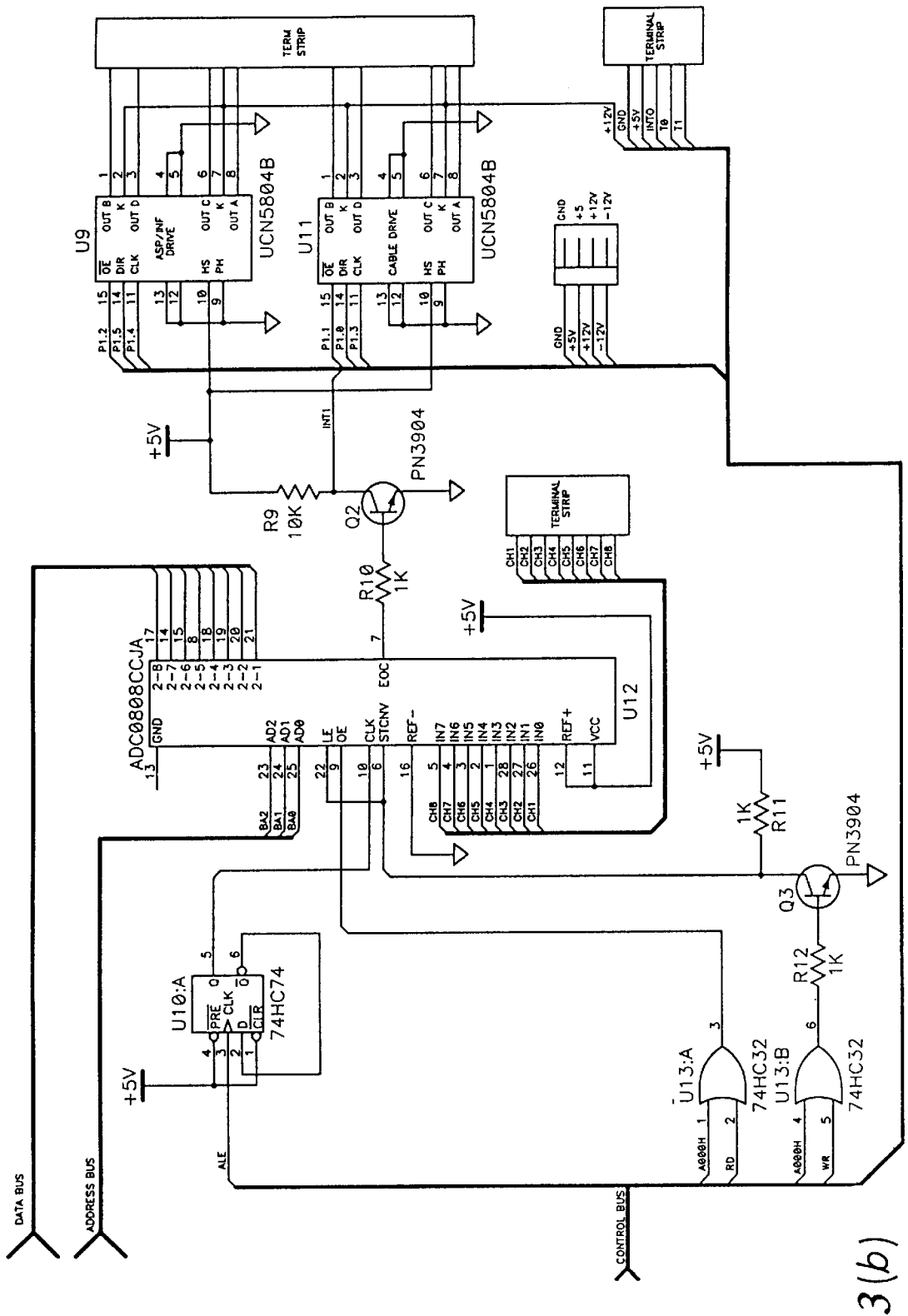
Figure 3C:
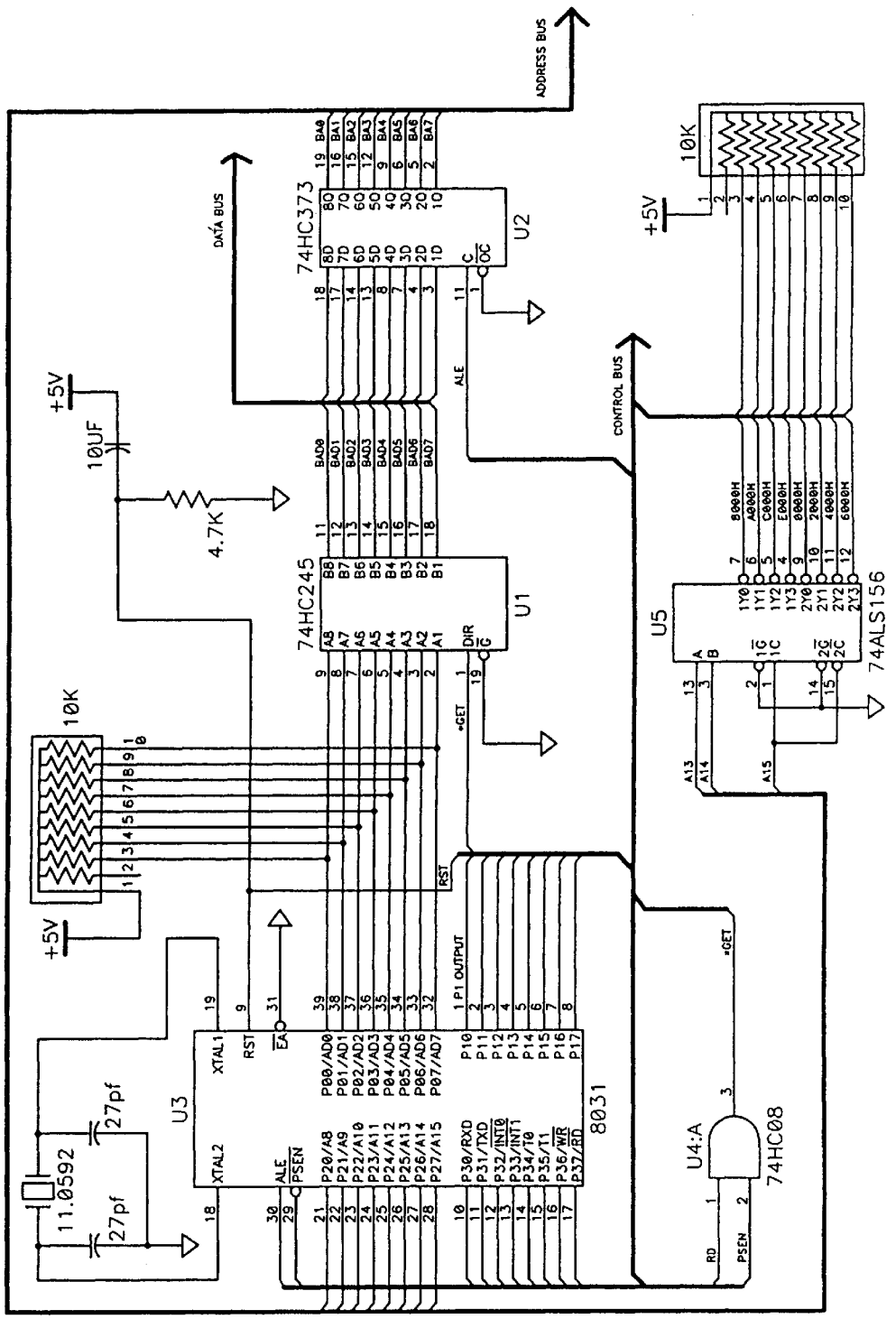
Figure 3D:
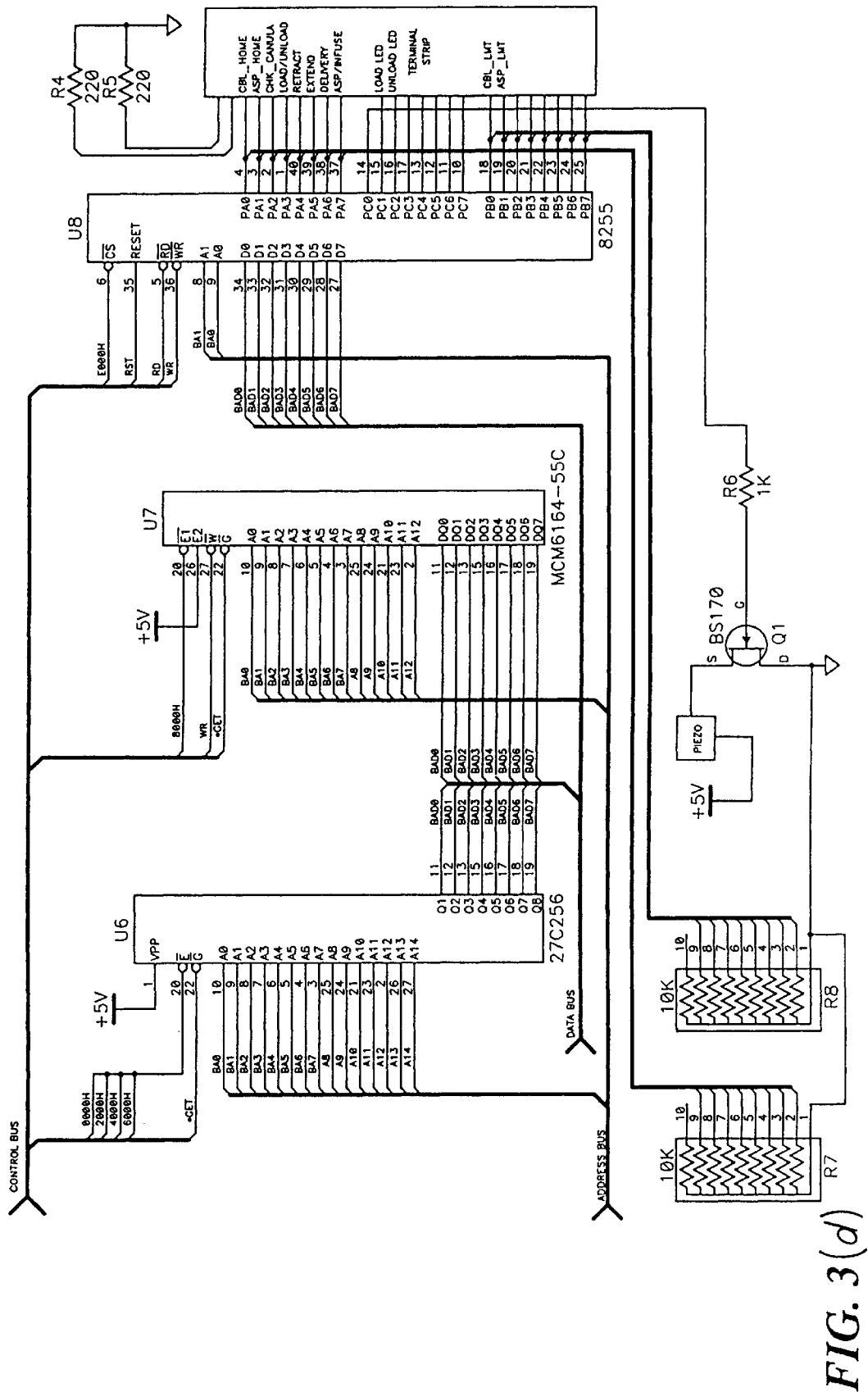
Figure 3E:
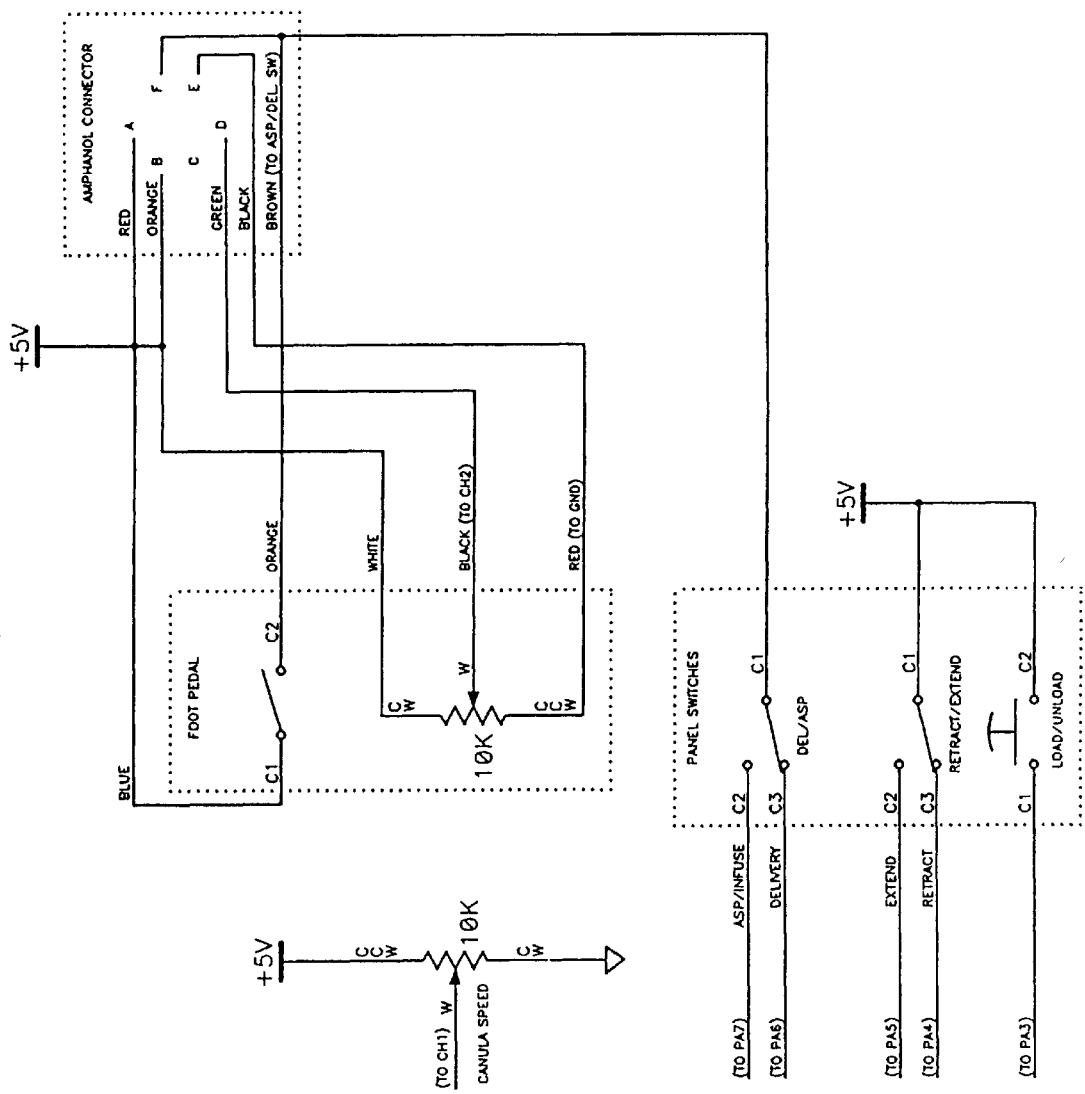

Referring now to FIGS. 1 and 2, a top view of a preferred embodiment of a microprocessor controlled electromechanical drive assembly 10 is shown. The assembly 10 includes stepper motors 12 and 14 (FIG. 2) which are contained within a housing 16. It should be noted that while an electromechanical drive is a preferred means for providing motive power, a mechanical drive mechanism obtains power from the energy stored in a spring or like mechanism may also be used. Attached to the housing 16 is a front panel 18 and a source of fluid pressure or suction in the form of a syringe 20, the fluid pressure or suction being controlled by stepper motor 14. The housing 16 can also contain a light source for illuminating a fiber optic filament as will be discussed later. A laser source could also be provided.

Both of the stepper motors 12 and 14 are controlled by a microprocessor 22. A plurality of switches and terminals are disposed on the front panel 18 to allow the operator to select the various functions and modes of operation used with the various functional attachments.

Power is selectively applied to the assembly 10 by power switch 24. DC power is supplied to the microprocessor by the transformer/rectifier assembly 26. The mode switch 28 allows the operator to alternate between actuation of the plunger 29 and the syringe 20. The plunger 29 is alternated between delivery and retraction by switch 30 which, depending on the position of the mode switch 28, also alternates the fluid pressure source, syringe 20, between infusion and aspiration. Thus in the embodiment of FIGS. 1 and 2, delivery or retraction of the plunger 29 is mutually exclusive of infusion or aspiration. In an alternative embodiment, infusion/aspiration can be performed simultaneously with delivery/retraction of the plunger 29. In either embodiment, separate conduits and associated drive means can be used to apply infusion and aspiration simultaneously to a functional attachment.

Pushbutton switch 32 controls the connecting and disconnecting of a functional attachment to device 10, with the connect status being indicated by LEDs 34. The delivery speed of the plunger 29 is infinitely variable over a range of speeds by speed control 36. The range of speeds is variable depending upon the exact procedure being performed and the associated functional attachment. The speed range can be altered if necessary to operate certain functional attachments. Actuation of the plunger 29 is controlled by footswitch 38 which may be a commercially available footswitch such as a model produced under the trademark Linemaster®. The footswitch 38 will operate the plunger 29 or the syringe 20 in the selected direction and speed as long as it is depressed.

Figure 4:
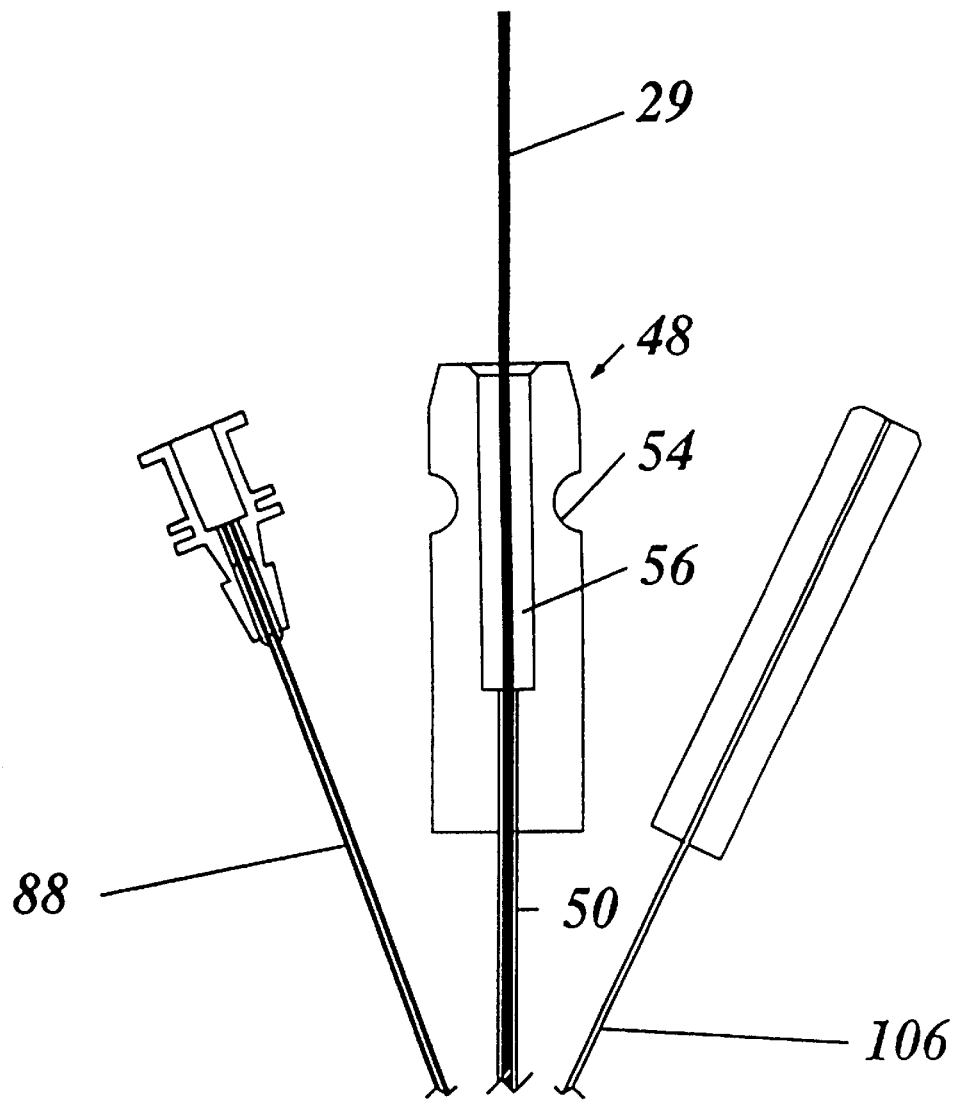
FIG. 4 is a partial sectional view of a handpiece cable assembly including fittings for the linear actuator, infusion line, and the fiber optic cable.
Figure 4:
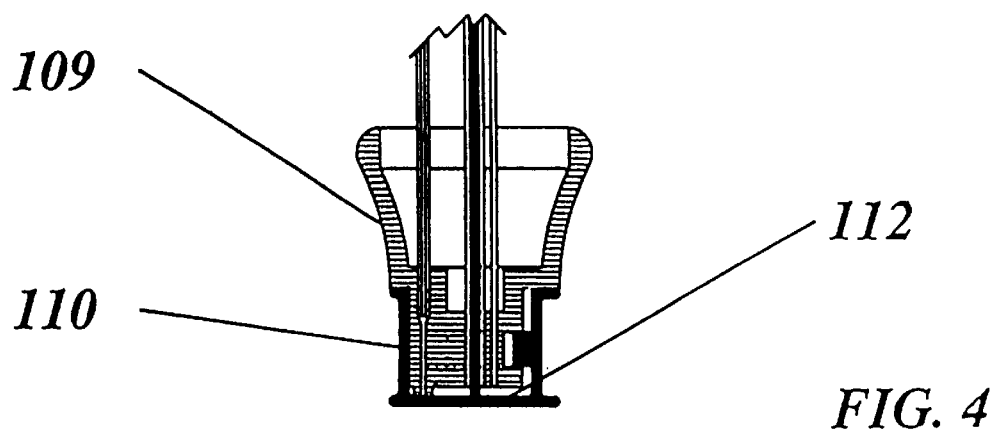

The assembly 10 includes an actuator 40 for advancing and retracting the plunger 29 which is connected to motor 12 via screw drive 42 and has solenoid controlled locking mechanisms 44 and 46. Locking mechanism 44 locks onto the connector 48 of sheath 50 and locking mechanism 46 locks onto the plunger 29. The connector 48 is adapted to be secured within terminal 52 when mechanism 44 locks onto annular recess 54 of the connector 48 (FIG. 4). The connector 48 has an axial bore 56 for slidably receiving the plunger 29. The sheath 50 is secured within the connector bore 56 by an adhesive, by frictional engagement, or is integrally attached. The opposite end of the sheath 50 is secured to a functional attachment. Thus, when locking mechanisms 44 and 46 are locked onto the connector 48 and plunger 29 respectively, movement of the actuator 40 causes movement of the plunger 29 within axial bore 56 and sheath 50 as the connector and sheath are held stationary relative to the actuator. Locking mechanism 46 moves with the actuator 40 along slide member 58.

Referring again to FIG. 2, the actuator travel 40 is limited by limit switches 60 and 62. The limit switches are actuated by transversely extending arm 64 and serve to physically limit the travel of the actuator 40 as well as interrupt the supply of power to stepper motor 12.

In a preferred embodiment, the syringe 20 is releasably mounted in syringe support 66. The support 66 includes a rectangular clamp 68 having a groove therein which is sized for holding the syringe 20. The clamp 68 has a threaded aperture extending therethrough, the aperture corresponding to an aperture in the support 66, both apertures aligned for receiving a screw 70 for tightening the clamp 68 onto the syringe 20. A recess 72 formed in the support is adapted to hold the annular flange 74 of the syringe 20 thereby preventing axial movement of the syringe. The syringe actuator 76 has a similar recess 78 for retaining the annular lip 80 at the tip of the syringe piston rod enabling the actuator to move the piston 82 to effect infusion or aspiration.

The syringe 20 is filled with infusion fluid from a second syringe 84 via 3-way stopcock 86. The stopcock 86 is positioned to allow fluid flow from second syringe 84 to syringe 20 at startup. The stopcock 86 is then repositioned to allow fluid flow or suction through infusion/aspiration terminal 87 to the infusion line 88.

The travel of actuator 76 is limited by actuator arm 77 and limit switches 90 and 92 in the same manner as actuator 40. It should be noted that the limit switches can be repositioned to adjust the travel of the actuators 40 and 76.

It should be noted that a pump, fluid reservoir, and a fluid collection container (not shown) may be used to apply fluid flow or aspiration to infusion line 88. A pump such as a peristaltic pump would provide suitable control of flow, and the infusion line 88 or other suitable conduit could be inserted into the pump drive mechanism. Such a pump could have the motor inside the housing of device 10, and have the pump and tubing connection external to the housing.

Referring now to FIG. 3, the microprocessor 22 circuitry is shown. Microcontroller U3 is the main control unit for the microprocessor 22. An Intel(R) 8031 may be used for U3. Microcontroller U3 is controlled in accordance with the following program.

---

```
File name: PG21.C
© Drummond Sci. Col. 5/94 Nick Di Trolio
Initialize controller
        Set time 0 (used for speed control)
        Enable interrupts
                Int0 used for clock pulses
                Int1 used for analog inputs
        Send output to P1 to initialize motor control function
        Small delay for solenoids to reset
        Output to I/O chip to initialize configuration (PortA=input; PortB=input; PortC=output)
        Read canula switch to determine in canula is present
                If canula is present, turn on load LED
                If canula is not present, turn on unload LED
        Move cable drive motor to home position (retracted)
                Load timer for set pulse width
                Set direction
                Enable motor drive
                Enable timer interrupt
                Enable timer
                        Send pulses to motor drive
                        Read cable home switch
                        loop until cable home switch is active
                Disable timer
                Disable timer interrupt
```

-continued

```
         Disable motor drive
         Beep once to indicate home
Move asp/infuse motor drive to home position (forward)
         Load timer for set pulse width
         Set direction
         Enable motor drive
         Enable timer interrupt
         Enable timer
                Send pulses to motor drive
                Read cable home switch
                loop until cable home switch is active
         Disable timer
         Disable timer interrupt
         Disable motor drive
         Beep twice to indicate home
Set infinite loop (main loop)
         read PortA to look for user command
                if load cable switch is pressed (on panel)
                       Read canula switch
                       If switch is on
                              Turn off load LED
                              Turn on unload LED (on panel)
                              Turn on canula latch solenoid
                              Delay 100ms.
                              Turn on cable latch solenoid
                              Read canula switch
                                     Loop until switch is off
                              Delay 5 seconds
                              Turn off cable latch solenoid
                              Delay 100ms.
                              Turn off cable latch solenoid
                       If switch is not active
                              Turn off unload LED
                              Turn on load LED
                              Move cable drive to home position
                              Turn on canula latch solenoid
                              Delay 100 ms.
                              Turn on cable latch solenoid
                              Read canula switch
                                     Loop until switch is on
                              Turn off canula latch solenoid
                              Delay 100ms.
                              Turn off cable latch solenoid
                       Return to main loop
                If cable forward switch (foot pedal) is pressed
                       Read analog voltage from potentiometer (on panel)
                       Use lookup table in memory to determine speed
                       Set motor direction
                       Enable cable motor drive
                       Enable timer
                       Enable interrupt
                              While cable forward switch is on:
                                     Read limit switch
                                     if limit switch is off:
                                            Pulse motor drive
                                     if limit switch is on
                                            Beep once
                                            wait until user releases foot pedal
                              Disable timer
                              Disable interrupt
                              Disable motor drive
                              Return to main loop
         If cable retract switch (on foot pedal) is on
                Read analog voltage from potentiometer (on panel)
                       Use lookup table in memory to determine speed
                       Set motor direction
                       Enable cable motor drive
                       Enable timer
                       Enable interrupt
                              While cable forward switch is on:
                                     Read limit switch
                                     if limit switch is off:
                                            Pulse motor drive
                                     if limit switch is on
                                            Beep once
                                            wait until user releases foot pedal
                              Disable timer
                              Disable interrupt
                              Disable motor drive
                              Return to main loop
```

-continued

```
If asp/infuse forward switch (on foot pedal) is on
        Read analog voltage from potentiometer (on foot pedal)
                Use lookup table in memory to determine speed
                Set motor direction
                Enable asp/infuse motor drive
                Enable timer
                Enable interrupt
                        While asp/infuse forward switch in on:
                                Read limit switch
                                if limit switch is off:
                                        Pulse motor drive
                                        Read analog voltage from potentiometer
                                        set timer registers from lookup table based on
                                        voltage
                                if limit switch is on
                                        Beep once
                                        wait until user release foot pedal
                                Disable timer
                                Disable interrupt
                                Disable motor drive
                                Return to main loop
If asp/infuse forward switch (on foot pedal) is on
        Read analog voltage from potentiometer (on foot pedal)
                Use lookup table in memory to determine speed
                Set motor direction
                Enable asp/infuse motor drive
                Enable timer
                Enable interrupt
                        While asp/infuse forward switch in on:
                                Read limit switch
                                if limit switch is off:
                                        Pulse motor drive
                                        Read analog voltage from potentiometer
                                        set timer registers from lookup table based on
                                        voltage
                                if limit switch is on
                                        Beep once
                                        wait until user release foot pedal
                                Disable timer
                                Disable interrupt
                                Disable motor drive
                                Return to main loop
```

U1 is a data latch which is used to latch data coming from U3 and may be a 74HC245 integrated circuit. U2 is also a data latch and may be a 74HC373 IC. U4 are 74HC08 Quad two input AND gates which are used as temporary data stores. U5 is a 74ALS156 decoder which outputs control signals from the controller U3 for control of the other ICs. U7 is a RAM which stores data such as speed control for access as needed by the controller U3. An MCM6164-55C 64K RAM may be used for U7. U13 are 74HC32 Quad two input OR gates. U8 is programmed to perform as 3 eight bit ports. Port A and Port B are used as inputs. Port C is used as an output. The inputs are from the panel switches or the limit switches in the control box. The outputs are indicators such as LEDs 311. U8 may be a 8255 IC and is controlled by U3.

U9 and U11 are UCN5804B microcontrollers and are used to drive the stepper motors 12 and 14. U9 and U11 respond to control signals from U3.

U12 is a ADC0808CCJA 8 bit A/D converter used to convert the input voltage from the footswitch to a digital format that the controller recognizes. U10 is a 74HC74 flip-flop which divides the clock pulse by 2 since U12 cannot convert data as fast as U3.

U14 is a 7407 hex buffer that responds to control signals from U3 to turn on the relays which activate the solenoids which operate locking mechanisms 44 and 46.

Thus, a drive means for a linear actuator which is capable of being operably connected to a functional attachment has been described.

A functional attachment capable of implantation of grafts, tissues, or drugs; as well as irrigation, aspiration or removal of tissue includes a handpiece cable assembly as is shown in FIG. 4. The handpiece cable assembly can be operatively connected to the microprocessor controlled drive assembly 10 and can be used for a retinal transplant procedure as described in our copending application 08/395,699 entitled "METHOD FOR TRANSPLANTATION OF PLANAR IMPLANTS AND SURGICAL INSTRUMENT THEREFOR" filed on even date herewith which is herein incorporated by reference.

Figure 5:
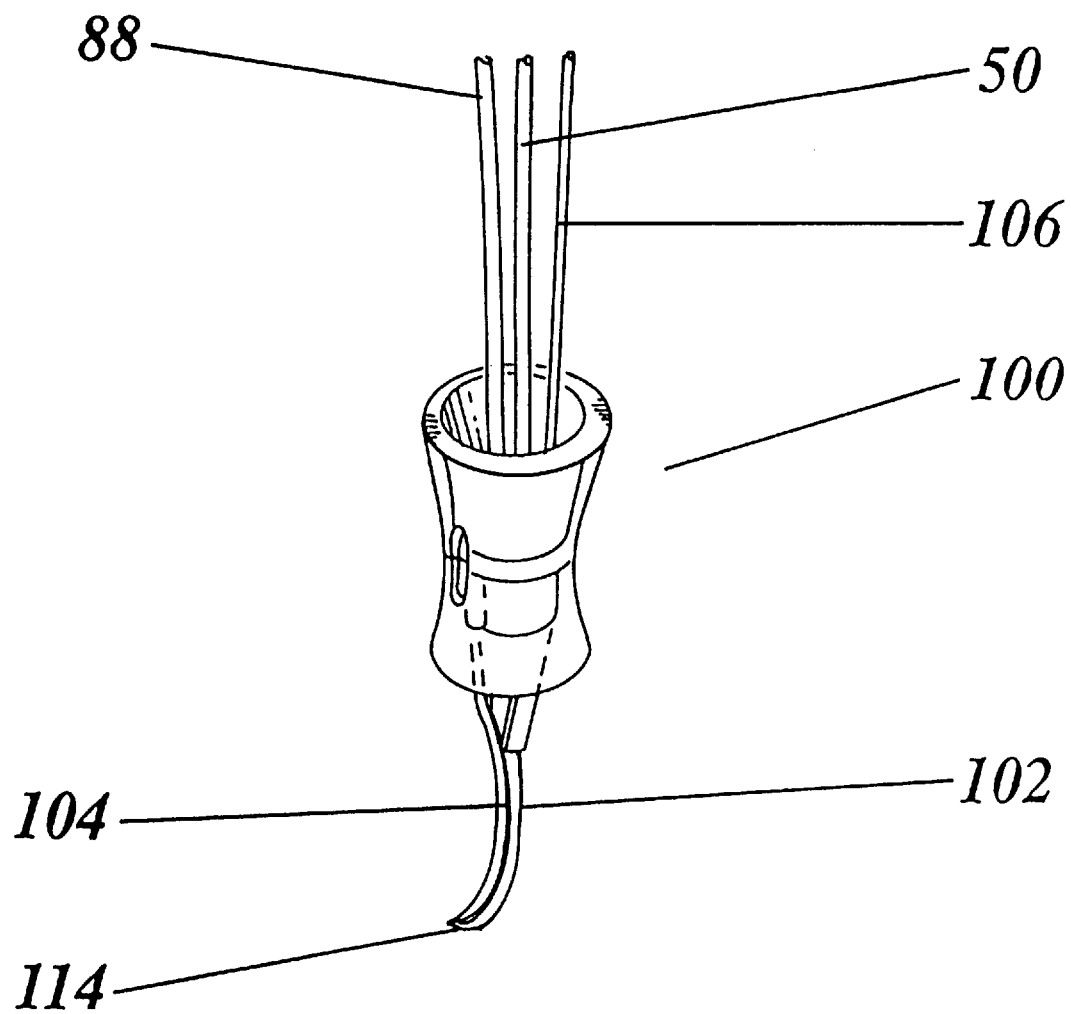
FIG. 5 is a perspective view of a functional attachment to the linear actuator of the present invention for containing an implant for implantation or for extraction of a material.

Referring now to FIG. 5, the handpiece cable assembly includes a handpiece 100 which is sectional and which has a delivery cannula 102 within which plunger 29 is axially movable to express the graft, drug, material, or device to be implanted. The handpiece 100 also includes an infusion lumen 104 which can be connected to infusion tube 88 for providing a source of infusion fluid or aspiration, as well as a fiber optic cable 106 which can be connected to a source of illumination for providing illumination at the site of implantation. Alternatively, a laser source can be connected to fiber optic cable 106 for, e.g., cauterizing blood vessels.

The sheath 50 is connected to the delivery cannula 102 to allow for passage of the plunger 29 into the delivery cannula for expressing the desired implant from the tubular tip 114 of the cannula.

In operation, the handpiece cable assembly is set up for the implantation of the graft by manually inserting the plunger 29 into and through the connector 48 and sheath 50 until the plunger enters a first section of the handpiece 100 and abuts the inner end wall 112 of the calibration cap 112 as shown in FIG. 4. The calibration cap 110 is adapted for detachable locking engagement with the first section of the handpiece 100 and is used to preset the initial position of the plunger 29 within the handpiece 100 when the actuator 40 is in the fully retracted position. Thus, the travel of the plunger 29 within the handpiece 100 extends from the preset position to a position of maximum extension within the delivery cannula 102 as determined by the spacing of the limit switches 60 and 62 as has been previously explained. The plunger 29 is made long enough so that an excess length of the plunger 29 protrudes from the connector 48 when the plunger abuts wall 112. The excess length of the plunger 29 is long enough to ensure proper engagement with the locking mechanism 46, but not so long as to prevent full insertion of the connector 48 into the terminal 52. To attach the handpiece assembly to the drive the connect/disconnect switch 32 is depressed thereby deactivating locking mechanisms 44 and 46 and returning the actuator 40 to the fully retracted position as shown in FIG. 2. The plunger 29 and connector 48 can then be inserted into terminal 52. It should be noted that for most procedures the limit switches 60 and 62 do not allow the plunger 29 to travel beyond the opening 114 of the tubular tip of the delivery cannula 102. When connector 48 is fully inserted into terminal 52 a switch (not shown) activates mechanisms 44 and 46 to lock onto annular recess 54 and plunger 29 respectively. Speed control 36 is then set to the desired speed. The foot pedal 38 can then be used to control extension or retraction of the plunger 29 as desired by setting the panel switches to the appropriate positions.

The infusion/aspiration assembly is set up by attaching syringes 20 and 84 to the infusion/aspiration terminal 87 with the syringe clamp 68 being firmly attached to the syringe 20 so as to prevent axial movement of the syringe 20. The syringe 20 is then loaded with infusion fluid from syringe 84 via stopcock 86 by setting the panel switches in the aspiration mode and depressing the foot pedal 38. The stopcock 86 is then repositioned to allow infusion fluid to flow through infusion line 88. Fluid pressure or suction can then be applied to infusion line 88 via microprocessor controlled stepper motor 14 by operating foot pedal 38 with the panel switches in the appropriate positions. It should be noted that a multilumen cannula can be attached to infusion line 88 to aspirate tissue from the subretinal space or other locations, followed by the implant of drugs, grafts, or devices.

The assembly can be adapted to provide accurately controlled motive power to a wide variety of functional attachments. Modification of the hardware or software may be required in order to operate certain functional attachments.

Figure 6B:
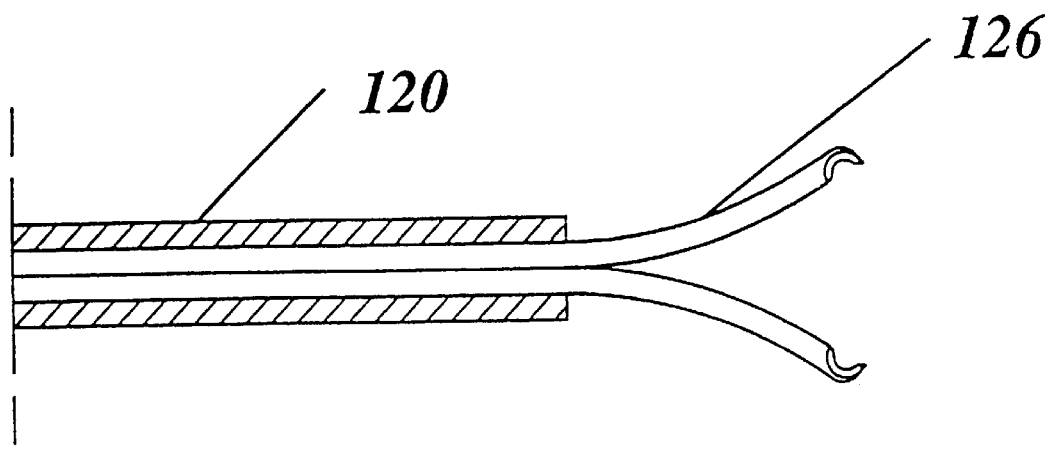
FIG. 6(b) is a sectional view of a functional attachment to the linear actuator of the present invention including grasping forceps which can be inwardly biased.
Figure 6A:
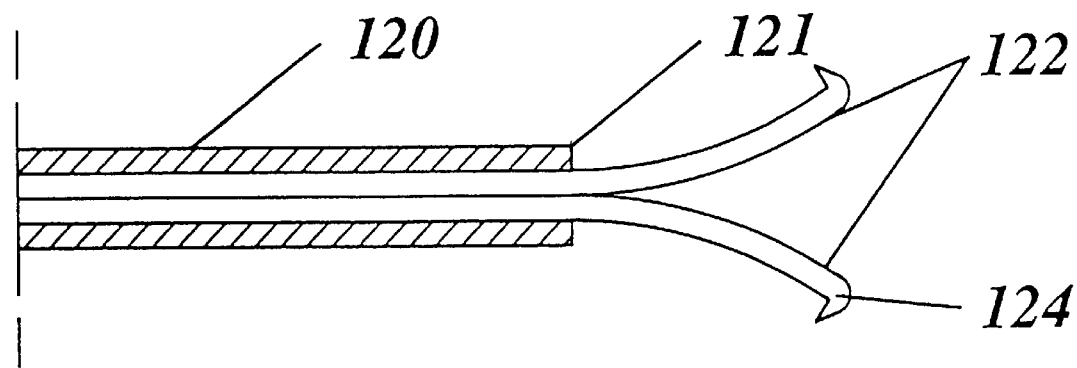
FIG. 6(a) is a sectional view of a functional attachment to the linear actuator of the present invention including grasping members which are outwardly biased.
Figure 6C:
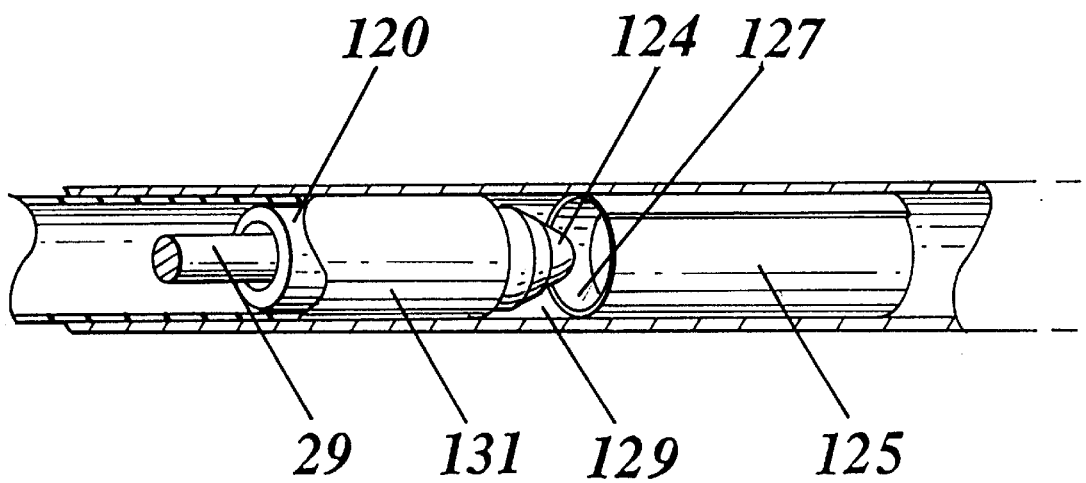
FIGS. 6(c) and 6(d) are views of a stent having an inner lip capable of engagement with the grasping membranes illustrated in FIG. 6(a).
Figure 6D:
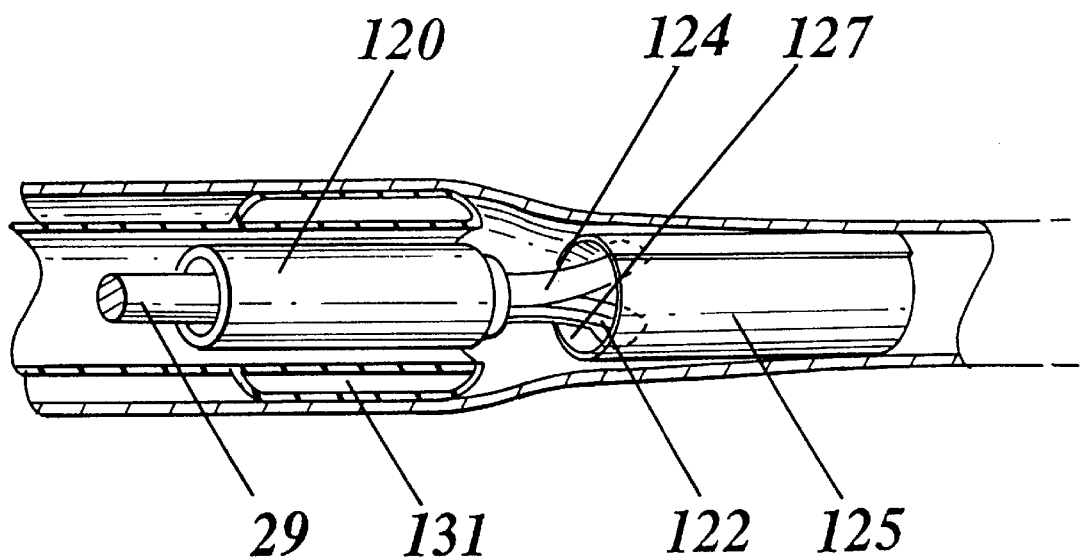

Another functional attachment capable of being operably connected to the drive assembly is shown in FIG. 6(a). This attachment requires the connection of a straight cannula 120 to the handpiece 100 which is sufficiently strong that it does not tear under the outward pressure exerted by retraction of outwardly biased members 122 into cannula 120. This may require reinforcement of tip 121, particularly in instances where cannula 120 is made sufficiently flexible to follow the contours of a blood vessel or other lumen into which it has been inserted. This attachment can be used as a stent retriever and has a pair of outwardly biased grasping members 122 having hook-like ends 124. The opposite ends of the grasping members 122 are attached to the plunger 29 by a connector (not shown) which allows for simultaneous delivery or retraction of the grasping members. When fully retracted, the grasping members 122, and ends 124, do not expand radially beyond the outer dimensions of the cannula 120 allowing for smooth progression of the device through blood vessels or other lumens. When advanced, the grasping members 122 extend outwardly as shown so that the ends 124 can be used to grasp the stent or other device for removal. (Examples of stents can be seen in U.S. Pat. No. 4,580,568 issued to Gianturco, U.S. Pat. No. 4,733,665 issued to Palmez, and U.S. Pat. No. 5,135,536, issued to Hillstead.) A stent 125 is illustrated in FIG. 6(c), and includes inner flexing lip 127 for engagement with ends 124. Inner flexing lip 127 is designed to lie against the inner surface of stent 125 when inserted so that blood flow biases lip 127 against the inner stent wall to create a smooth surface.

Although two members 122 are shown, additional members may be connected to plunger 29 and be biased radially outward to ensure a better grip and manipulation of the stent. The blood vessel may be dilated in from of stent 125, for example at position 129 with a balloon dilatation catheter 131 to permit use of the cannula and grasping elements of the device shown in 6(a) to be inserted through a lumen passing through the balloon dilatation catheter into the stent 125 as shown in FIG. 6(a) and permitting retraction of the stent 125 into the lumen of the balloon dilatation catheter.

A forceps-like grasping attachment is shown in FIG. 6(b). This attachment may be used for removal of tissues or devices, or for the manipulation of various devices within the body, and is attached to the drive assembly 10 in the same manner as the attachment of FIG. 6(a). The attachment has grasping members 126 which are biased outwardly to open upon advancement of the plunger 29 and to close upon retraction thus allowing the attachment to be used as a miniature forceps.

In one embodiment, the forceps can be inserted through a retinotomy to perform a choroidal biopsy; the members 126 (which can be two or more in number) may also be rotatably connected to plunger 29, and means for rotating members 126 in order to ensure a cleaner incision, or a better cutting and tearing action. A cauterization device (e.g. electrocauterization probe) can be included to reduce bleeding following the excision of tissue to biopsied and its retraction within cannula 120.

The device can be used for insertion into a lumen of a balloon dilatation catheter for removal of a pre-shrunken (e.g., thermally cooled) stent, or may be used to both radially contract and extract a vascular stent. The cannula 120 in both attachments can be provided with an infusion/aspiration lumen which can be used for irrigation/aspiration at the surgical site.

It should be noted that the devices in FIGS. 5 and 6 can be effectively employed by making only small surgical incisions.

Figure 7:
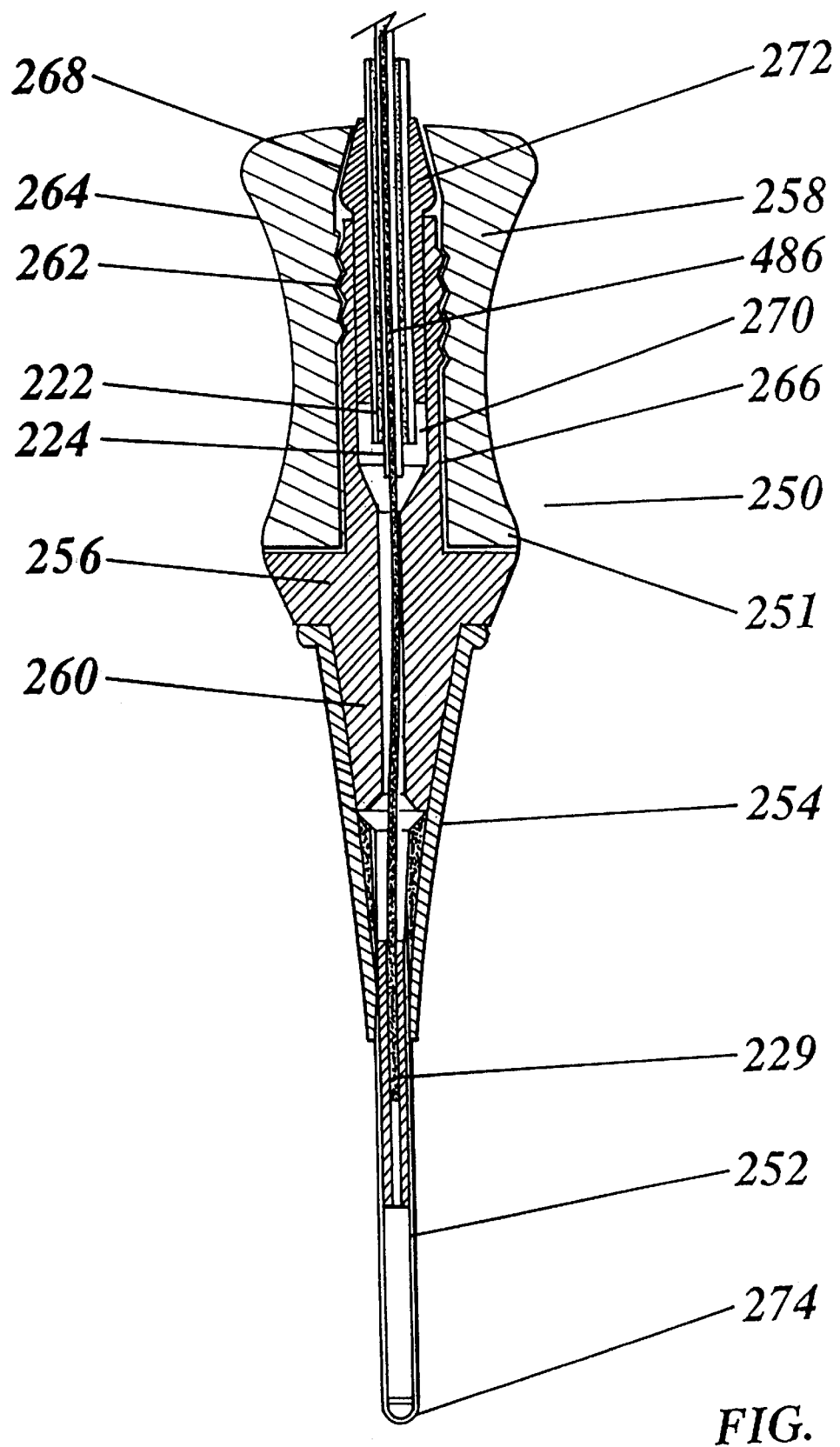
FIG. 7 is a sectional view of a handpiece cable assembly which can be operably connected to a source of motive power.

A handpiece cable assembly 250 having a handpiece 251 which can be functionally attached to a source of motive power is shown in FIG. 7. The handpiece cable assembly 250 includes a delivery cannula 252 which is secured to hollow frusto-conical connector 254 by an adhesive. The main body of the assembly 250 has an inner member 256 and an outer member 258. The inner member 256 has a frusto-conical portion 260 projecting from one end and a threaded cylindrical post 262 projecting from the opposite end. Connector 254 is adapted for frictional engagement with projecting portion 260 and may be further secured thereto by an adhesive. Outer member 258 has a contoured outer surface 264 to facilitate manipulation of the delivery cannula. A central aperture 266 in the outer member is threaded to enable threaded engagement with post 262 and is inwardly sloped at one end to form a camming surface 268. The post 262 has an aperture 270 adapted to receive a vice member 272 which has an exterior camming surface thereby forming a pin vice assembly comprised of threaded post 262, outer member 258, and vice member 272. Thus, axial movement of the syringe tube 222 within the handpiece 251 is restricted by tightening the pin vice assembly, which causes vice member 272 to compress syringe tube 222 and sheath 224.

If desired infusion/aspiration can be manually effected by securing an infusion/aspiration lumen (not shown) to the exterior of the delivery cannula 252 by using an adhesive, the infusion lumen having an opening proximate the opening at the tip 274 of the delivery cannula, the infusion/aspiration lumen being connected to a syringe 276.

In another embodiment, plunger 29 may be actuated by a foot pedal operated ratchet assembly shown as a rectangular box in FIG. 2. The ratchet assembly includes two foot pedals, one for delivery, the other for retraction, or a single foot pedal having a directional switch, which reverses the direction of movement of the plunger in response to one up/down cycle of the foot pedal. The travel per foot pedal cycle can also be adjusted. The plunger 29 will move with each depression of the foot pedal until it reaches its limit of travel, the distance traveled by a single depression being adjustable by the spacings of gear teeth on the ratchet assembly as is well known. Such a ratchet drive assembly may be included with the device 10 as a backup source of motive power.

Figure 8:
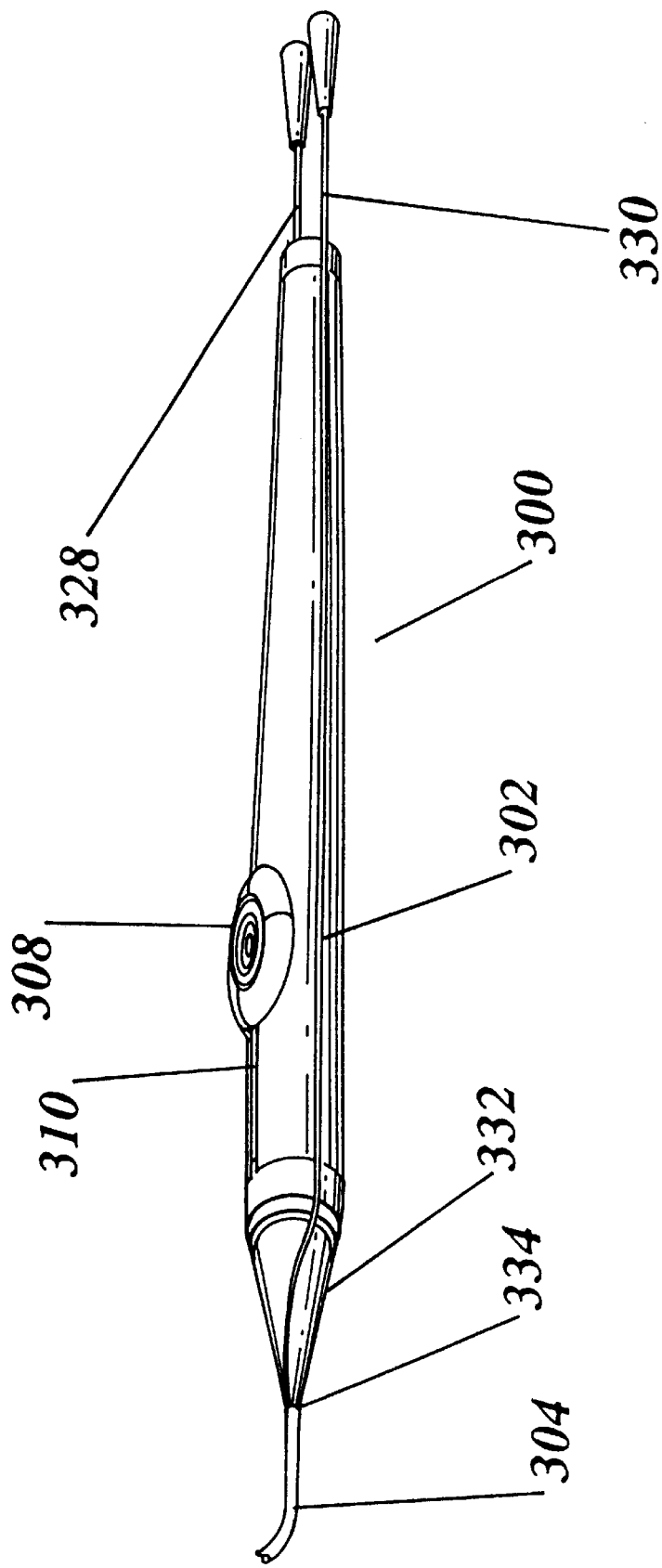
FIG. 8 is a perspective view of an alternative hand actuated embodiment of the surgical instrument.
Figure 9:
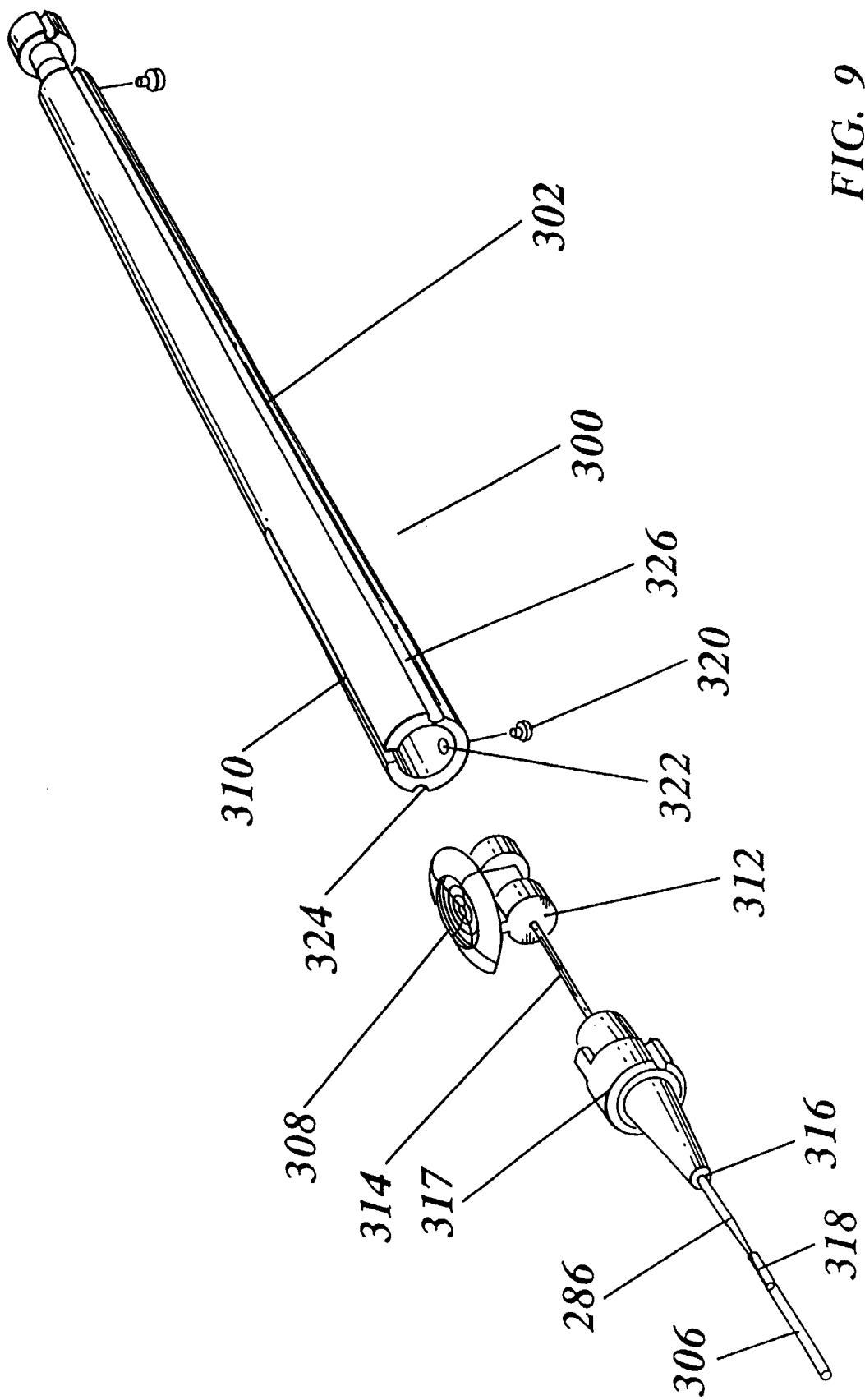
FIG. 9 is a partially exploded perspective view of FIG. 8.

Manual delivery and retraction of a linear actuator can be accomplished with an alternative embodiment as shown in FIGS. 8 and 9. In this embodiment the attachment 300 comprises a cylindrical aluminum housing 302 having a delivery cannula 304 attached thereto. A plunger 306 is actuated by thumbswitch 308 which slides in track 310. An actuator 312 is connected to thumbswitch 308 as can be seen in FIG. 12. Actuator 312 is connected to plunger 306 by rod 314 which projects into and through bore 316 in luer connector 317 and is inserted into an aperture 318 at one end of plunger 306 where it is secured therein by an adhesive. Luer connector 317 is connected to the housing 302 and therefore is held stationary relative to rod 314, actuator 312 and plunger 306. The travel of plunger 306 is limited by set screw 320 which screws into bore 322 and projects into the path of actuator 312. A plurality of bores such as bore 322 can be provided to adjustably limit the travel of actuator 312 and therefor the plunger 306. Grooves 324 and 326 are provided to hold infusion conduits 328 and 330 in place. Infusion fluid or aspiration can be provided to the infusion conduits 328 and 330 by a syringe.

The delivery cannula 304 is connected to a hollow frusto-conical connector 332 which is secured to housing 302 and has a bore 334 into which the delivery cannula 304 is secured by an adhesive. Conduits 328 and 330 can also be secured to the exterior surfaces of connector 332 and delivery cannula 304 as shown to provide aspiration/infusion at the tip of the delivery cannula. Advancing or retracting the thumbswitch causes advancing or retraction of the plunger 306 within the delivery cannula 304. For further information on the preferred uses and applications of the present invention,, reference may be made to copending U.S. patent applications 08/322,735, 08/057,144, 08/033,105, and the At page 16, line 23, replace "application entitiled" with U.S. patent application Ser. No. 08/395,699, entitled "METHOD FOR PREPARATION AND TRANSPLANTATION OF PLANAR IMPLANTS AND SURGICAL INSTRUMENTS THEREFOR", FILED ON EVEN DATE HEREWITH.

Of course, two or more of the features described with respect to the alternate embodiments could be combined, as necessitated by the particular circumstances.

As various changes could be made in the above surgical instruments, compositions of matter and methods without departing from the scope of the invention, it is intended that all matter contained in the above description or shown in the accompanying drawings shall be interpreted as illustrative and not in as limiting.

What is claimed is:

1. A device for surgical delivery, manipulation, and extraction of surgical material and devices, comprising:
   a source of motive power;
   a cannula having a tip with an opening therein, said tip being insertable into a patient to permit surgical delivery, manipulation, and extraction of material and devices;
   a plunger having first and second end portions, said first end portion connected to said source of motive power, said source of motive power capable of selectively imparting linear motion to said plunger, means for adjusting the speed of said plunger and the direction of travel of said plunger, said plunger capable of being partially disposed within said cannula so that said second end may linearly move within said cannula; means to limit said linear motion of said plunger with respect to said cannula, said limit means being adjustable;
   wherein a plurality of functional attachments can be operably connected to or engaged by said second end portion one at a time to deliver, manipulate, cut, or extract via said opening of said cannula in operable relation with the motion of said plunger, wherein, when said functional attachment is an implant contained within said cannula and said cannula is to be used to deliver an implant into a patient, said tip is insertable into the patient, and said second end of said plunger can be extended into said cannula to cause the expression of said implant into the patient.

2. The device of claim 1 where said source of motive power is microprocessor controlled.

3. The device of claim 1 including means to provide a source of infusion fluid to said functional attachments.

4. The device of claim 3 where said means to provide a source of infusion fluid is microprocessor controlled.

5. The device of claim 1 including means to provide a source of aspiration to said functional attachments.

6. The device of claim 5 where said means to provide a source of aspiration is microprocessor controlled.

7. The device of claim 1 including means to provide a source of illumination to said functional attachments.

8. The device of claim 1 where said source of motive power is a manually actuated thumbswitch.

9. The device of claim 1 where said source of motive power is a manually operated ratchet assembly.

10. The device of claim 1, wherein said source of motive power is an electromechanical drive.

11. The device of claim 1, further comprising a functional attachment comprising at least two members extending from said second end portion of said plunger, each of said members having a proximal end and a distal end, wherein said proximal ends are operably connected to said plunger, and the distal ends of said members are biased radially outward and capable of reciprocating radial movement in response to reciprocating linear movement of said plunger, said cannula having a distal end, said members extending radially outward upon at least partial extension of said members from said distal end of said cannula.

12. The device of claim 11, wherein said members are adapted for cutting tissue upon at least partial linear retraction of said members into the distal end of said cannula from a relatively more extended position.

13. The device of claim 12, wherein said members are adapted for grasping a stent disposed within a blood vessel upon at least partial linear extension of said members from the distal end of said cannula.

* * * * *